(12) United States Patent
Arric

(10) Patent No.: US 10,896,750 B2
(45) Date of Patent: Jan. 19, 2021

(54) SYSTEMS AND METHODS FOR MEDICATION MANAGEMENT

(71) Applicant: Arrix, Inc., Irvine, CA (US)

(72) Inventor: James Arric, Irvine, CA (US)

(*) Notice: Subject to any disclaimer, the term of this patent is extended or adjusted under 35 U.S.C. 154(b) by 0 days.

(21) Appl. No.: 15/961,805

(22) Filed: Apr. 24, 2018

(65) Prior Publication Data

US 2019/0326006 A1  Oct. 24, 2019

(51) Int. Cl.
  *G16H 20/13* (2018.01)
  *G16H 10/60* (2018.01)
  *A61J 7/04* (2006.01)
  *B65D 83/04* (2006.01)
  *G16H 80/00* (2018.01)

(52) U.S. Cl.
  CPC ............ *G16H 20/13* (2018.01); *A61J 7/0454* (2015.05); *A61J 7/0481* (2013.01); *B65D 83/0409* (2013.01); *G16H 10/60* (2018.01); *G16H 80/00* (2018.01)

(58) Field of Classification Search
  CPC ........ G16H 20/13; G16H 10/60; G16H 80/00; A61J 1/03; A61J 1/14; A61J 7/0427; A61J 7/0481; A61J 2200/70; A61J 7/0069; A61J 7/0436; A61J 7/0084; A61J 1/22; A61J 7/00; B65D 83/00; B65D 83/0005; B65D 83/0038; B65D 83/0016; B65D 83/0077; B65D 83/0083; B65D 83/0409; B65D 83/0436; B65D 83/0454
  USPC .............................. 221/190, 153, 258, 208, 2
  See application file for complete search history.

(56) References Cited

U.S. PATENT DOCUMENTS

| | | | | | |
|---|---|---|---|---|---|
| 1,610,717 | A | * | 12/1926 | Teabout | G07F 11/44 221/152 |
| 1,982,917 | A | * | 12/1934 | Lothrop | G01F 11/24 222/153.09 |
| 2,134,180 | A | * | 10/1938 | Felber | B65D 83/0409 221/200 |
| 2,204,821 | A | * | 6/1940 | Priddy | B65D 83/0409 222/336 |
| 3,122,278 | A | * | 2/1964 | Crozier | A47J 47/01 222/305 |
| 3,161,321 | A | * | 12/1964 | Mellion | A47F 1/10 221/266 |
| 3,276,636 | A | * | 10/1966 | Johnson, Jr. | B65D 83/0409 222/368 |

(Continued)

*Primary Examiner* — Rakesh Kumar
(74) *Attorney, Agent, or Firm* — Cionca IP Law P.C.; Marin Cionca

(57) ABSTRACT

A medication management system, having a pill dispensing system having: a funnel having an open bottom end; a tube holder; a tube having: a hollow interior; means for securing the tube to the tube holder, such that a rotational movement of the tube holder causes a same rotational movement of the tube; a pill receiving hole facing upwards when the pill dispensing system is not actuated, and providing access to the hollow interior; wherein the open bottom end is aligned with the pill receiving hole when the pill dispensing system is not actuated, such that the pill receiving hole is configured to receive a pill, the pill dropping from the funnel into and housed within the hollow interior; and means for causing the rotational movement, such that the pill receiving hole faces downwards and thus dispenses the pill housed within the hollow interior out of the pill dispensing system.

8 Claims, 35 Drawing Sheets

(56) References Cited

U.S. PATENT DOCUMENTS

| | | | | |
|---|---|---|---|---|
| 3,312,377 A * | 4/1967 | Chuhran | A47G 19/34 | 222/359 |
| 3,318,491 A * | 5/1967 | Williamson | B65D 83/0409 | 222/363 |
| 3,610,468 A * | 10/1971 | Borsum | B65D 83/049 | 221/256 |
| 3,659,754 A * | 5/1972 | Barone | A01K 5/0275 | 222/368 |
| 3,830,411 A * | 8/1974 | Krechmar | B65D 83/0418 | 222/363 |
| 4,162,751 A * | 7/1979 | Hetland | G01F 11/24 | 222/293 |
| 4,189,066 A * | 2/1980 | Berghahn | B65D 83/0409 | 221/266 |
| 4,285,448 A * | 8/1981 | Group | G01F 11/24 | 222/368 |
| 4,428,502 A * | 1/1984 | Veltri | B65D 83/0409 | 221/152 |
| 4,522,313 A * | 6/1985 | Jennings | B65D 83/0409 | 206/540 |
| 4,569,463 A * | 2/1986 | Pellegrino | A47G 19/34 | 222/185.1 |
| 4,828,143 A * | 5/1989 | Jennings | B65D 83/0409 | 221/266 |
| 4,852,767 A * | 8/1989 | Humphrey | G07F 11/08 | 221/241 |
| 4,887,738 A * | 12/1989 | Jennings | B65D 83/0409 | 221/264 |
| 4,957,219 A * | 9/1990 | Robbins | A47G 19/34 | 222/368 |
| 5,375,744 A * | 12/1994 | Henderson | B65G 65/4881 | 222/306 |
| 5,437,393 A * | 8/1995 | Blicher | A47F 1/03 | 141/369 |
| 6,112,942 A * | 9/2000 | Deacon | B65D 83/0409 | 221/155 |
| 6,267,265 B1 * | 7/2001 | Issa | A61J 7/0076 | 221/263 |
| 6,308,860 B2 * | 10/2001 | Eagle | B65D 83/0409 | 221/131 |
| 6,991,134 B2 * | 1/2006 | Bailey | A47J 43/22 | 222/158 |
| 7,017,780 B2 * | 3/2006 | Renaud | B65D 83/0409 | 221/263 |
| 7,216,776 B2 * | 5/2007 | Gelardi | B65D 83/0409 | 221/256 |
| 7,648,037 B2 * | 1/2010 | Ohashi | B65D 47/30 | 215/301 |
| 7,703,639 B2 * | 4/2010 | Landau | A47G 19/34 | 222/1 |
| 7,726,354 B2 * | 6/2010 | Shlomo | B65B 31/047 | 141/65 |
| 8,141,727 B2 * | 3/2012 | Gruenwald | B65D 23/12 | 215/6 |
| 9,434,528 B2 * | 9/2016 | Ashbaugh | B65D 83/0409 | |
| 9,903,746 B2 * | 2/2018 | Rusch | G01F 11/24 | 222/153.09 |
| D851,500 S * | 6/2019 | Han | D9/726 | |
| 2005/0115632 A1* | 6/2005 | Haimi | B65B 31/047 | 141/65 |
| 2006/0231566 A1* | 10/2006 | Indig | G07F 11/44 | 221/266 |
| 2006/0266764 A1* | 11/2006 | Bieger | G07F 11/44 | 221/263 |
| 2010/0065577 A1* | 3/2010 | Coughlin | G07F 11/32 | 221/277 |
| 2010/0181279 A1* | 7/2010 | Gruenwald | B65D 23/12 | 215/201 |
| 2011/0060457 A1* | 3/2011 | De Vrught | A61J 1/03 | 700/241 |
| 2015/0166247 A1* | 6/2015 | Ashbaugh | B65D 83/0409 | 221/265 |

* cited by examiner

SYSTEMS AND METHODS FOR MEDICATION MANAGEMENT

BACKGROUND OF INVENTION

1. Field of the Invention

The invention relates generally to medication and more specifically to medication dispensing and tracking.

2. Description of the Related Art

In recent years, chronic disease has been on the rise. Due to this, adults, particularly adults over 50, may have to take medication daily. As an example, many people need to take up to four medications on a daily basis. Thus, there is a potential for adverse drug reactions (or adverse drug effects), which can be caused by improper use of medication, allergic reactions, and under-doses and overdoses, to become more prevalent. Adverse drug reactions can be caused by a number of reasons, such as by many different medications having a similar appearance and causing confusion to a user. Another problem that is associated with prescription medication is that typically, manual entry of information is needed to capture medication, provider, patient, and pharmacy information when generating a prescription. This can be a multi-step process which can be time-consuming or inefficient. Another problem that may be associated with prescription medication is that doctors, when performing medication reconciliation, may be only able to rely on word of mouth from a patient, which may be unreliable or inaccurate.

Therefore, there is a need for a solution to these problems.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, a system and method are provided for medication management, wherein a medication management platform is accessed through a mobile device application.

In an aspect, a system and method are provided for medication management wherein a medication management platform is accessed through a mobile device application, and is in communication with a medication dispenser, wherein the medication dispenser is compact and transported by the user such that the user can access their medication at any time, and wherein the dispensing of medication from the dispenser is tracked and recorded by the medication management platform, and wherein the medication dispenser displays an alert to the user when medication consumption is needed.

In an aspect, a system and method are provided for medication management, wherein medication is delivered to a user, at the prescribed dose and at the prescribed time, by using a mobile application and a medication delivery apparatus, which are both used to scan information about medications using optical character recognition (OCR) technology that automatically reads and imports medication name, type, and instructions, along with patient, provider, and pharmacy information, and wherein the medication delivery apparatus is used to dispense medication. The medication may be prescription medication. The system may be provided with audio or visual alerts to notify a user that medication is due, or issue warnings to the user, such as potentially harmful drug-drug or drug-food interactions, or allergy warnings. The user, family members, and doctors may be notified if a dose is missed by the user. The medication delivery apparatus may also be provided with a video screen for face-to-face calls which the user may use if assistance is needed, for example. The system may also provide information and education, social networking, and downloads related to the medication, which may be accessed through the mobile application or through the apparatus. The mobile application may be provided with a platform for medication reconciliation, which may allow doctors to discontinue and/or update any medications already prescribed and stored at home. Doctors may also make changes to prescriptions immediately by using the medication management system through the mobile application or the apparatus. Thus, an advantage is that medication regimens may be safer and more reliable, and more efficient for a user, and the user is not required to remember or memorize their prescription schedules or dosages, or any other similar information. Another advantage is that a user is alerted or prompted to take their medication, and may reduce the risk of missed dosages. Another advantage is that prescriptions may be created or changed more easily and efficiently by a doctor. Another advantage is that the OCR may allow a user, doctor, pharmacist, or any other individual to easily, efficiently, and quickly scan and import data such as medication, provider, patient, and pharmacy information.

In an aspect, a medication management system is provided, comprising a pill dispensing system having: a funnel for storing medication, the funnel having: an open top end; and an open bottom end, wherein the open top end is larger than the open bottom end; a tube holder having: a first tube holder end; a second tube holder end; a fin extending between the first tube holder end and the second tube holder end; wherein the first tube holder end is associated with a gear wheel; a tube having: a hollow interior; a first tube end; a second tube end; a channel extending between the first tube end and the second tube end, the channel being configured to receive the fin when the tube slides into the tube holder, and the channel being configured to restrict a side-to-side movement of the tube within the tube holder when the first tube end is aligned with the first tube holder end and the second tube end is aligned with the second tube holder end, such that the tube is secured to the tube holder, and such that a rotational movement of the tube holder causes a same rotational movement of the tube; a pill receiving hole between the first tube end and the second tube end, the pill receiving hole facing an upwards direction when the pill dispensing system is not actuated, and the pill receiving hole providing access to the hollow interior; wherein the open bottom end is aligned with the pill receiving hole when the pill dispensing system is not actuated, such that the pill receiving hole is configured to receive a pill of the medication, wherein the pill drops from the funnel into and is housed within the hollow interior; wherein the tube is removable from the tube holder by sliding the tube in a lengthwise direction away from the tube holder; and a rack and pinion actuator for actuation of the pill dispensing system, wherein: a rack of the rack and pinion actuator is at least a gear arm; a pinion of the rack and pinion actuator comprises the gear wheel; and a gear arm actuator is configured to move the pinion, thus causing the rotational movement of the tube holder due to the association of the tube holder with the gear wheel; such that the rotational movement causes the pill receiving hole to face a downwards direction and thus dispense the pill housed within the hollow interior out of the pill dispensing system. Again, an advantage is that medication regimens may be safer and more reliable, and more efficient for a user, and the user is not required to remember or memorize their prescription schedules or dosages, or any other similar information. Another advantage is that a user is alerted or prompted to take their medication, and may reduce the risk of missed dosages. Another advantage is that prescriptions may be created or changed more easily and efficiently by a doctor. Another advantage is that the OCR may allow a user, doctor, pharmacist, or any other individual to easily, efficiently, and quickly scan and import data such as medication, provider, patient, and pharmacy information.

In an aspect, a medication management system is provided, comprising a pill dispensing system having: a funnel having: an open top end; and an open bottom end, wherein the open top end is larger than the open bottom end; a tube holder having: a first tube holder end; and a second tube holder end; a tube having: a hollow interior; a first tube end; a second tube end; means for securing the tube to the tube holder when the first tube end is aligned with the first tube holder end and the second tube end is aligned with the second tube holder end, such that a rotational movement of the tube holder causes a same rotational movement of the tube; a pill receiving hole between the first tube end and the second tube end, the pill receiving hole facing an upwards direction when the pill dispensing system is not actuated, and the pill receiving hole providing access to the hollow interior; wherein the open bottom end is aligned with the pill receiving hole when the pill dispensing system is not actuated, such that the pill receiving hole is configured to receive a pill dropping from the funnel into and be housed within the hollow interior; and means for causing the rotational movement of the tube holder, such that the rotational movement causes the pill receiving hole to face a downwards direction and thus dispense the pill housed within the hollow interior out of the pill dispensing system. Again, an advantage is that medication regimens may be safer and more reliable, and more efficient for a user, and the user is not required to remember or memorize their prescription schedules or dosages, or any other similar information. Another advantage is that a user is alerted or prompted to take their medication, and may reduce the risk of missed dosages. Another advantage is that prescriptions may be created or changed more easily and efficiently by a doctor. Another advantage is that the OCR may allow a user, doctor, pharmacist, or any other individual to easily, efficiently, and quickly scan and import data such as medication, provider, patient, and pharmacy information.

In an aspect, a method of medication management is provided, using a pill dispensing system comprising a pill dispensing system having: a funnel having: an open top end; and an open bottom end, wherein the open top end is larger than the open bottom end; a tube holder having: a first tube holder end; and a second tube holder end; a plurality of tubes, each tube of the plurality of tubes having: a hollow interior; a first tube end; a second tube end; means for securing the tube to the tube holder when the first tube end is aligned with the first tube holder end and the second tube end is aligned with the second tube holder end, such that a rotational movement of the tube holder causes a same rotational movement of the tube; a pill receiving hole between the first tube end and the second tube end, the pill receiving hole facing an upwards direction when the pill dispensing system is not actuated, and the pill receiving hole providing access to the hollow interior; wherein the open bottom end is aligned with the pill receiving hole when the pill dispensing system is not actuated, such that the pill receiving hole is configured to receive a pill, wherein the pill drops from the funnel into and is housed within the hollow interior; wherein the tube is removable from the tube holder by sliding the tube in a lengthwise direction away from the tube holder; and means for causing a rotational movement of the tube holder, such that the rotational movement causes the pill receiving hole to face a downwards direction and thus dispense the pill housed within the hollow interior out of the pill dispensing system, such that the rotational movement causes the pill receiving hole to face a downwards direction and thus dispense the pill housed within the hollow interior out of the pill dispensing system; and a medication management platform accessible through an electronic device; the method comprising the steps of: receiving a set of written instructions related to a medication regimen using a first medication; a medication management platform accessible through an electronic device comprising at least a camera; the method comprising the steps of: receiving a set of written instructions related to a medication regimen using a first medication; accessing the medication management platform through the electronic device; using the at least a camera of the electronic device to read the set of written instructions; importing the medication regimen into a user record stored within a medication management platform database; sending the medication regimen to the pill dispensing system; providing a user with the plurality of tubes, each tube of the plurality of tubes having a unique pill receiving hole; receiving directions from the medication management platform for selection of a tube of the plurality of tubes, wherein the pill receiving hole of the selected tube matches a size of a pill of the first medication; inserting the selected tube into the tube holder; and actuating the pill dispensing system after a notification is sent to the user via the medication management platform; dispensing the pill out of the pill dispensing system. Again, an advantage is that medication regimens may be safer and more reliable, and more efficient for a user, and the user is not required to remember or memorize their prescription schedules or dosages, or any other similar information. Another advantage is that a user is alerted or prompted to take their medication, and may reduce the risk of missed dosages. Another advantage is that prescriptions may be created or changed more easily and efficiently by a doctor. Another advantage is that the OCR may allow a user, doctor, pharmacist, or any other individual to easily, efficiently, and quickly scan and import data such as medication, provider, patient, and pharmacy information.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which:

FIGS. 15A-15B show examples of user interfaces of a physician's portal of the medication management platform showing a detailed view of an individual patient under the user's care, according to an aspect.

FIGS. 17A-17B show examples of user interfaces of a physician's portal of the medication management platform wherein a medication reconciliation view shows conflicting medication warnings and prescription details to the user, according to an aspect.

DETAILED DESCRIPTION

Figure 1A:
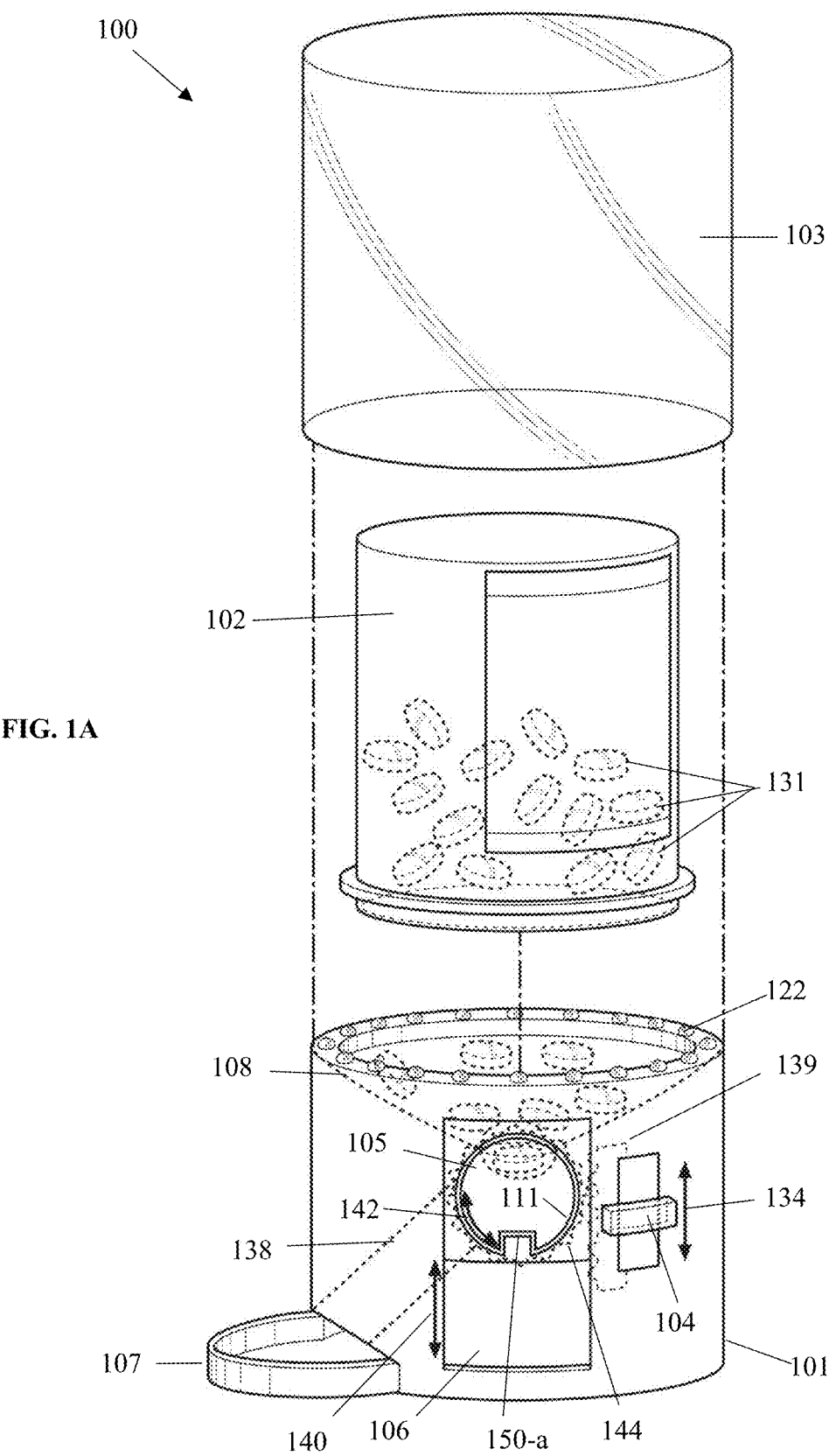
FIGS. 1A-1B illustrate the exploded right side view and the exploded left side view, respectively, of a compact medication dispensing apparatus, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

As used herein and throughout this disclosure, the term "mobile device" refers to any electronic device capable of communicating across a mobile network. A mobile device may have a processor, a memory, a transceiver, an input, and an output. Examples of such devices include cellular telephones, personal digital assistants (PDAs), portable computers, etc. The memory stores applications, software, or logic. Examples of processors are computer processors (processing units), microprocessors, digital signal processors, controllers and microcontrollers, etc. Examples of device memories that may comprise logic include RAM (random access memory), flash memories, ROMS (read-only memories), EPROMS (erasable programmable read-only memories), and EEPROMS (electrically erasable programmable read-only memories). A transceiver includes but is not limited to cellular, GPRS, Bluetooth, and Wi-Fi transceivers.

"Logic" as used herein and throughout this disclosure, refers to any information having the form of instruction signals and/or data that may be applied to direct the operation of a processor. Logic may be formed from signals stored in a device memory. Software is one example of such logic. Logic may also be comprised by digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network.

Mobile devices communicate with each other and with other elements via a network, for instance, a cellular network. A "network" can include broadband wide-area networks, local-area networks, and personal area networks. Communication across a network can be packet-based or use radio and frequency/amplitude modulations using appropriate analog-digital-analog converters and other elements. Examples of radio networks include GSM, CDMA, Wi-Fi and BLUETOOTH.® networks, with communication being enabled by transceivers. A network typically includes a plurality of elements such as servers that host logic for performing tasks on the network. Servers may be placed at several logical points on the network. Servers may further be in communication with databases and can enable communication devices to access the contents of a database. For instance, an authentication server hosts or is in communication with a database having authentication information for users of a mobile network. A "user account" may include several attributes for a particular user, including a unique identifier of the mobile device(s) owned by the user, relationships with other users, call data records, bank account information, etc. A billing server may host a user account for the user to which value is added or removed based on the user's usage of services. One of these services includes mobile payment. In exemplary mobile payment systems, a user account hosted at a billing server is debited or credited based upon transactions performed by a user using their mobile device as a payment method.

For the following description, it can be assumed that most correspondingly labeled elements across the figures (e.g., 111 and 211, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

Figure 1B:
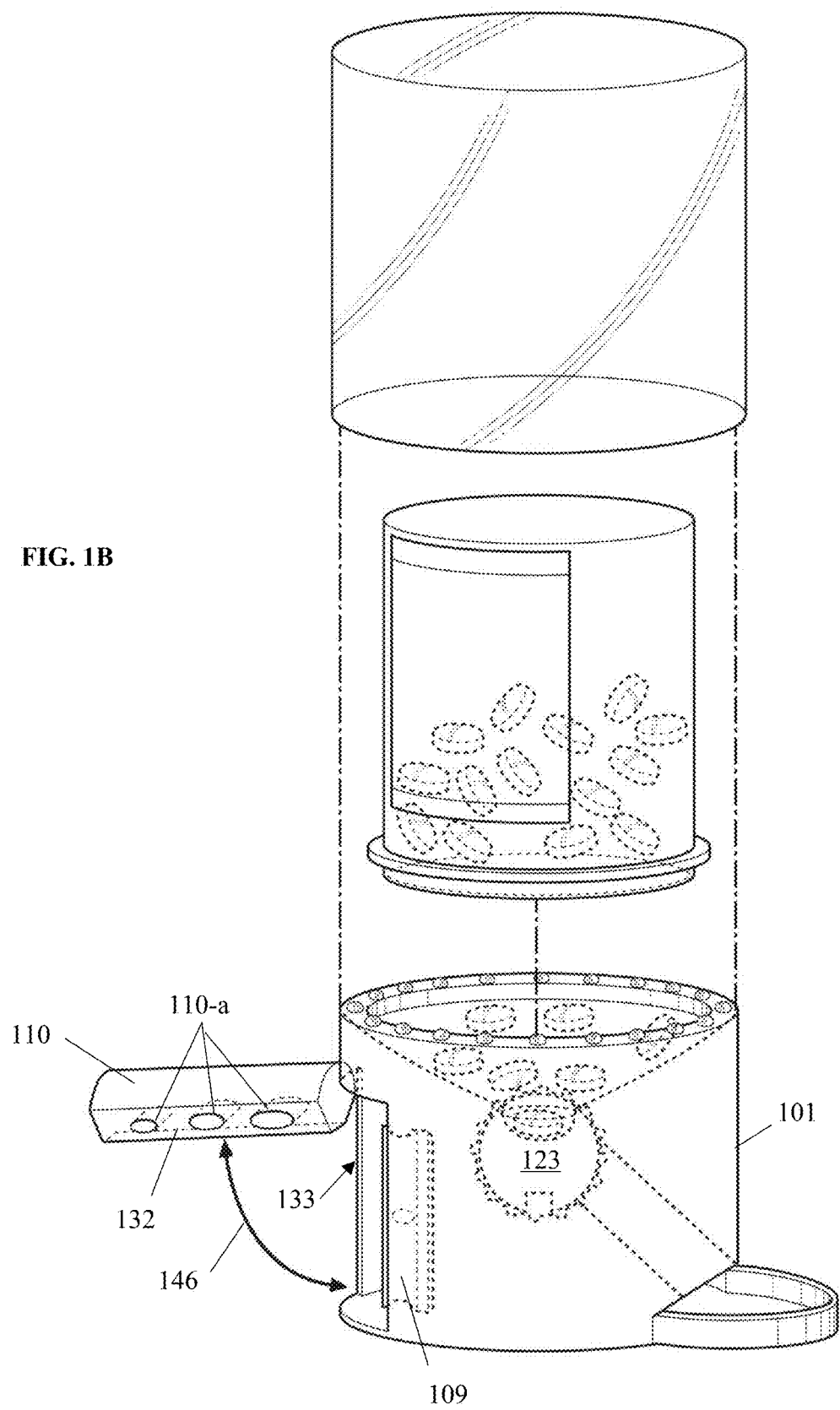

FIGS. 1A-1B illustrate the exploded right side view and the exploded left side view, respectively, of a compact medication dispensing apparatus ("medication dispensing apparatus," "compact dispenser," "compact medication dispenser" "medication delivery apparatus," "medication dispenser," "dispensing apparatus," or "apparatus") 100, according to an aspect. An exemplary medication bottle 102 is also shown in these views. As an example, a medication dispenser may be provided in a travel-sized, miniature, or compact configuration as shown in FIGS. 1A-1B, or may be provided in a tabletop configuration, as will be discussed further when referring to FIGS. 7A-7C. The compact dispenser 100 may be provided with a base 101, onto which the medication bottle ("medication bottle," "medicine bottle," or "bottle") 102 may be secured, and next covered by a glass casing 103. The glass casing 103 may, for example, be magnifying, and provide 3× magnification, and may provide 360 degrees of magnification around the bottle 102 such that the prescription labels can be easily read by the user.

Figure 2A:
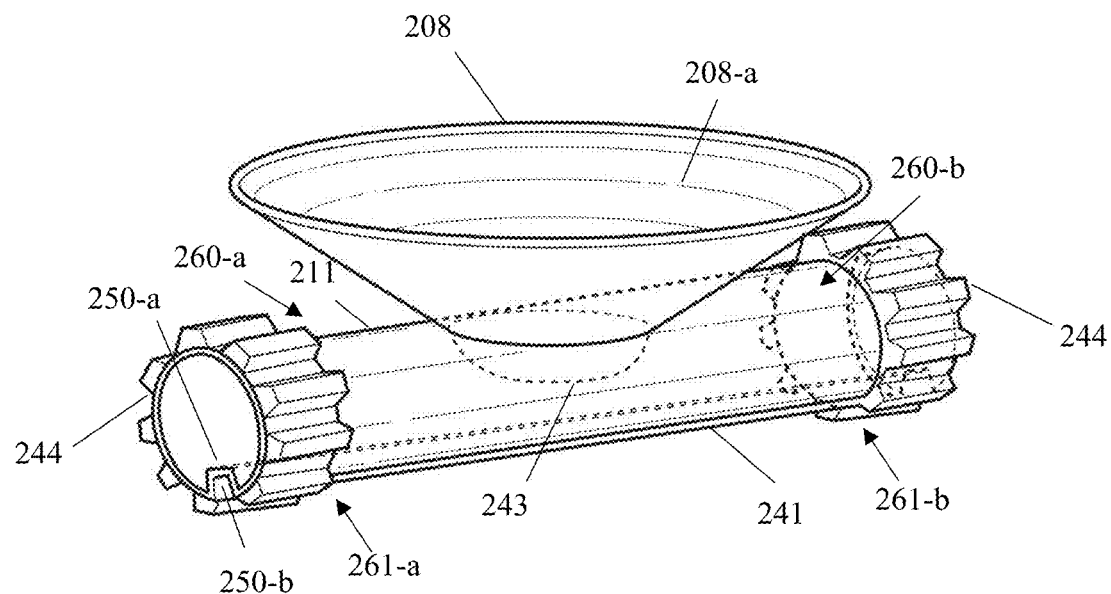
FIGS. 2A-2C illustrate the side perspective view, the top plan view, and an exploded view of the funnel, the pill tube, and the pill tube of a medication dispensing apparatus, according to an aspect.
Figure 2B:
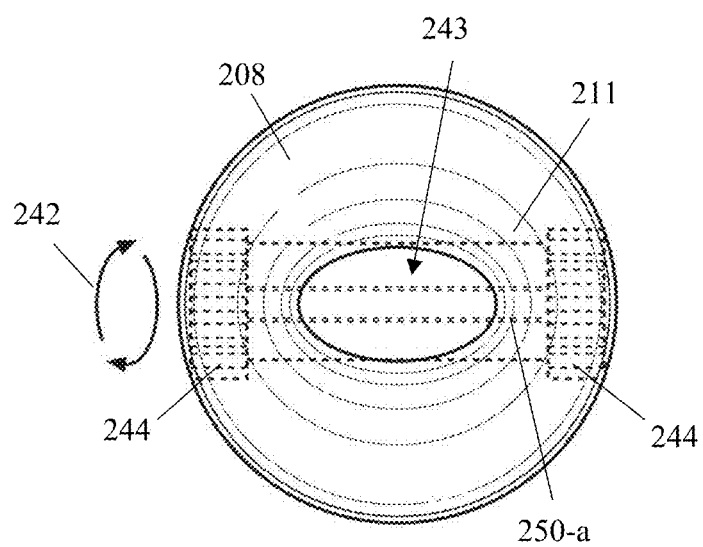

The compact dispenser 100 may be provided with a pill dispensing system ("pill dispensing system" or "medication dispensing system"), having a funnel 108, a pill tube and pill tube holder (as will be further discussed when referring to FIGS. 2A-2B), and a rack and pinion system wherein the rack is a gear arm 139, and the pinion is a gear (as shown by 244 in FIGS. 2A-2B). The pill dispensing system may also be provided with a gear actuator. The gear actuator may, for example, be a dispensing lever ("dispensing lever," or "lever") 104. The bottle 102 may be secured to the funnel 108 of the pill dispensing system within the compact dispenser 100. The bottle 102 may attach securely to the base 101 securely with childproofing means, such as, for example, with a mechanism requiring a push-down action for removing or securing the bottle 102. The removal of the bottle 102 may thus requiring pushing down and twisting simultaneously.

When a user receives medication and wishes to use the medication with the medication dispenser, first, the user may import the medication information into the medication management platform by any suitable means. For example, the user may manually enter the information, download the information, or scan the prescription label such that the label can be read by optical character recognition (OCR) technology. After the import is completed, the medication management system may, based upon the size and shape of the medication being used, recommend one pill tube ("pill tube" or "tube") 111 of a plurality of pill tubes provided with the pill dispensing system, to be secured to the pill dispensing system. Each pill tube 111 may include a pill tube hole sized to match a particular type of pill. The base 101 may be provided with a tube receiving slot ("receiving slot or "tube receiving slot") 105 on a first side of the surface of the base, and the receiving slot may be used for receiving the pill tube 111 into the base. The base 101 may be configured to securely hold the pill tube 111 by providing a sliding door 106 on the first side of the surface of the base, and by being closed on an opposite second side of the surface of the base. As an example, the base may also be provided with rubber grip feet (not shown).

The user may then begin use of the medication with the medication dispenser, such as the compact dispenser 100 as shown, and insert the selected pill tube 111 into the medication dispenser 100 by carrying out the following exemplary process. First, the user unscrews a cap provided with the medication bottle 102, and secures the bottle 102 onto the funnel 108 by turning the medication dispenser 100 upside-down onto the mouth of the bottle 102. Next, the sliding door 106 is opened by unlocking the door 106 through, for example a pushing action, which may unlatch the door, and sliding the door in a direction. The sliding door may be movable in the directions indicated by arrow 140, for example. The follow actions may be performed with the medication dispenser 100 upside-down such that the pills or medication 131 from the bottle 102 are not released out of the bottle. Next, the pill tube 111 is inserted into the receiving slot 105 by aligning the groove 150-$a$ of the pill tube 111 with the fin of the tube holder (shown in FIG. 2A). Next, the pill tube is pushed as far back as possible by the user pushing on a first end of the tube, until the tube reaches the opposite side of the base 101, where a second end of the pill tube 111 is in contact with a release button 123. Next, the pill tube 111 is securely held within the housing by closing the sliding door 106 on the first end of the tube 111 by moving the sliding door 106 upwards, while the second end is resting against the release button 123 on the side of the base 101 opposite of the sliding door 106. The sliding door 106 may be held in place by, for example, a latch or any other suitable means of holding the door in place. The sliding door 106 may closed off the opening of the receiving slot 105, and the pill tube 111 may be held against the wall of the base 101 having the release button 123 on the opposite side, thus preventing the pill tube 111 from being released or falling out of the medication dispenser 100. The medication dispenser 100 may then be turned right-side-up for use, and a pill 131 may release from the bottle 102 through the funnel 108 and into the pill tube 108.

Next, when the medication 131 is needed by the user, the user operates the dispenser 100 by actuating a lever 104 in a direction indicated by arrow 134. The movement of the lever 104 may cause a movement of a rack or gear arm 139, which may actuate the rotational movement of a pinion or gear 144. The rotational movement of the gear 144 may then next cause the pill tube, which may be associated with the gear 144, to also rotate, such as in the directions indicated by arrows 142. Next, the rotational movement of the pill tube 111 may cause a hole in the pill tube (as will be further discussed when referring to FIGS. 2A-2C) to face downwards and release the pill within the tube into an exit tube 138 and cause the pill to fall into a pill catcher 107 such that the pill 131 is accessible by the user.

The lever 104 or any other suitable means for actuating the pill dispensing system may be provided with safety features such as a locking mechanism, for example, to provide a means of child-proofing or locking the medication 131 within the dispensing apparatus 100. As an example, the lever 104 may be provided with a lock requiring a user to push the lever in a particular direction in order to unlocked and moved. It should be understood that any suitable means may be used to provide a child-proofing or safety feature to the pill dispensing system of the dispenser 100 that also allows a user convenient and easy access to their medication.

When a bottle 102 is to be changed for a new bottle or a refill, or the pill tube 111 needs to be changed for any other purpose, the pill tube 111 may be removed from the base 101 by carrying out the following exemplary process. The sliding door 106 may be moved to expose the pill tube 111. Next, the user pushes the release button 123 which causes the pill tube 111 to protrude out of the receiving slot 105. Next, the pill tube 111 is removed completely out of the base 101.

Again, the compact dispenser 100 may, for example, be operated for dispensing pills by moving the lever 104, which the user may slide up or down in the directions indicated by arrow 134 as shown as an example. As an example, the lever 104 may be associated with a rack and pinion actuator or any other suitable means causing a rotation of the pill tube to catch a pill from the funnel 108. The dispensed pill may then be released from the compact dispenser 100 through the exit tube 138, and next fall into the pill catcher 107.

Lights 122, which may be RGB LED lights, for example, may be used as indicators or notifications to the user, such as when it is time to dispense a pill, such as by the exemplary process described above. Exemplary alerts or notifications that the lights 122 may be used for may include drug interactions, drug allergies, a scheduled pill consumption, the need for a drug refill, and other such similar notifications or warnings. The dispenser may be provided with a built-in battery or similar power source having a circuit board to power the LED lights and communicate with, for example, a mobile device.

As shown in FIG. 1B, the compact dispenser 100 may be provided with a pill cutting carrier ("pill carrier," "pill cutting carrier," "cutting carrier," or "carrier") 110, which may be used for cutting pills. The pill carrier 110 may be provided with a cutting hole or a plurality of cutting holes 110-a, which may be different sizes to accommodate different types or sizes of pills or other medication. The carrier may be associated with the base 101 of the compact dispenser 100, and may be associated with the base 101 by a hinge, for example. The carrier 110 may thus swing outwards from the base 101 and back inwards, such as in the directions indicated by arrows 146, and provide access to the cutting holes 110-a when out of the base 101. The carrier 110 may be housed in the base 101 when the carrier 110 is pushed back into a carrier slot 133 within the base 101. As an example, the carrier 110 may be released from the base 101 or locked back into the base 101 by a pushing action and may be locked in by a latch, for example. The base 101 may also house a cutting blade or razor 109, which may fit into a razor slot 132 of the carrier 110 when the carrier 110 is inserted into the carrier slot 133, thus causing the razor 109 to pass through the pills within the cutting holes 110-a and cutting the pills into halves. The user may then release the carrier 110 from the carrier slot 133, and remove the cut pills from the cutting holes 110-a.

Figure 2C:
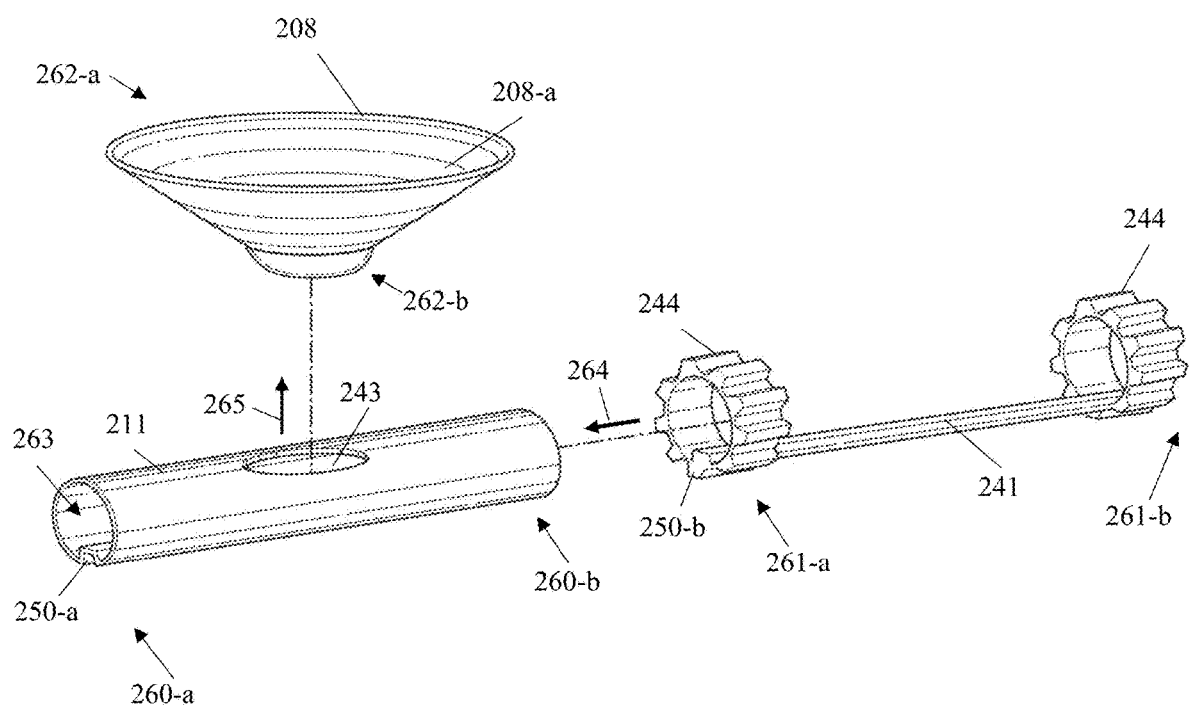
Figure 7A:
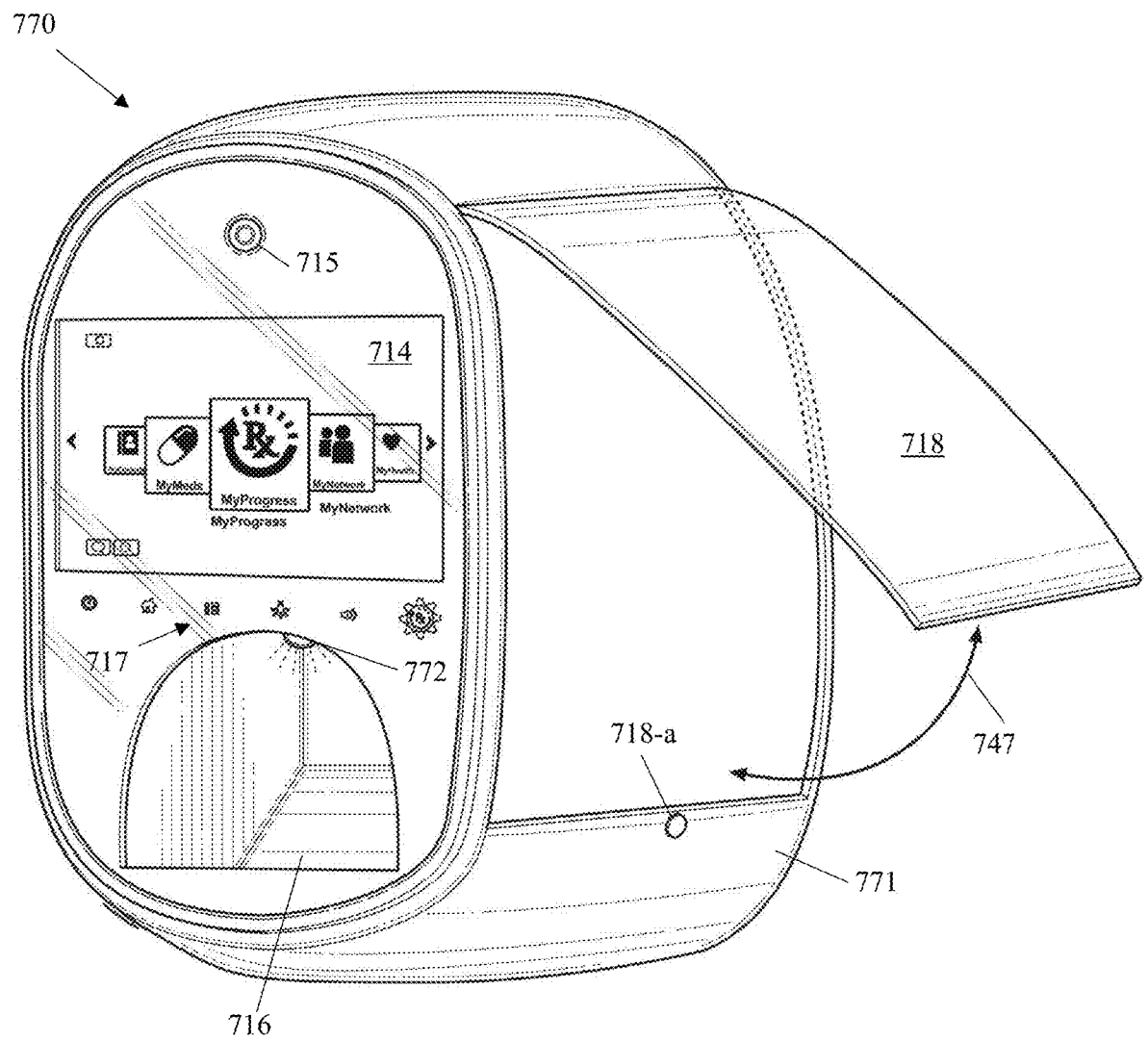
FIGS. 7A-7C illustrate the front perspective view, the front view, and the sectional top view, respectively, of another example of the medication dispensing apparatus, according to an aspect.
Figure 7B:
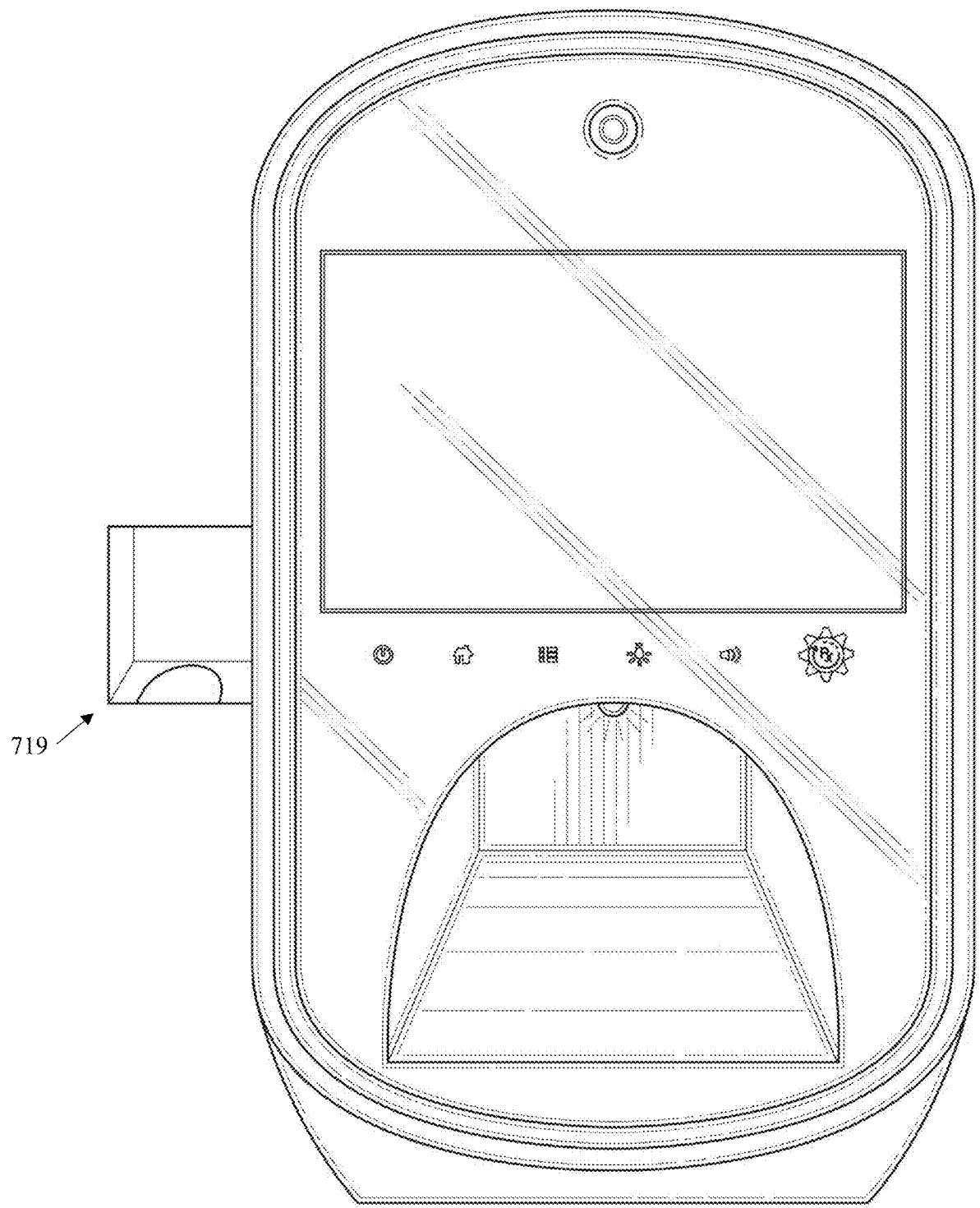
Figure 7C:
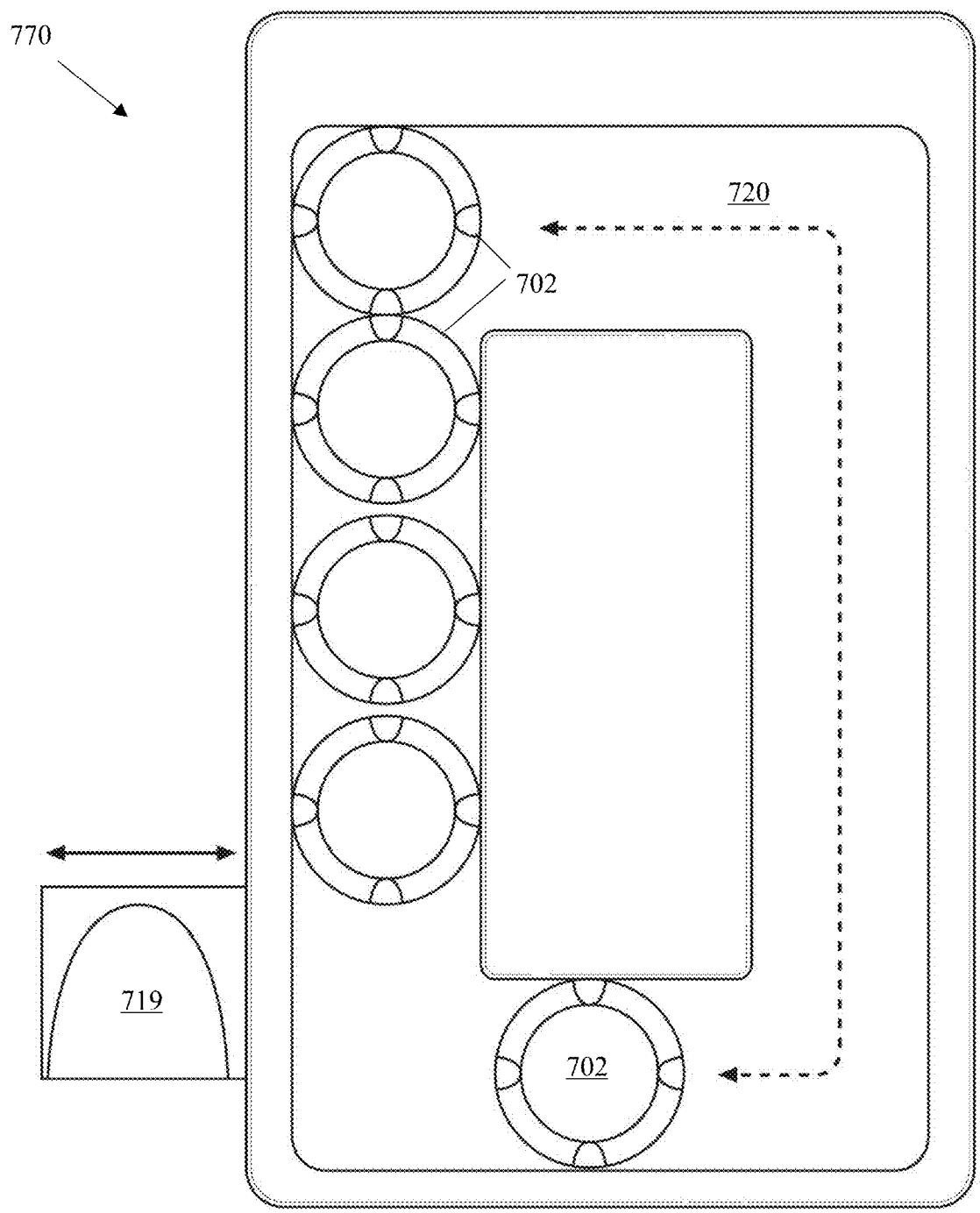

FIGS. 2A-2C illustrate the side perspective view, the top plan view, and the exploded view of the funnel 208, the pill tube ("pill tube" or "tube") 211, and the pill tube holder ("pill tube holder" or "tube holder") 241 of a medication dispensing apparatus, according to an aspect. As an example, a pill dispensing system using a funnel 208, a pill tube 211, and a pill tube holder 241 may be used with a compact or travel-size medication dispenser as shown in FIGS. 1A-1B, or may be used with a tabletop medication dispenser, as shown in FIGS. 7A-7C, or any other suitable medication dispensing apparatus.

The funnel 208 may be provided with threads 208-a such that a medicine bottle (as shown by 102 in FIG. 1A) may be screwed onto the funnel, or the funnel 208 may as another example be provided with channels for the bottle to rest in. Additionally, the funnel 208 may be provided with an open top end 262-a and an open bottom end 262-b, wherein the open top end is larger than the open bottom end, as shown in FIG. 2C. The pill tube 211, having a first end 260-a and a second end 260-b, may be cylindrical with a hollow interior 263 to hold a pill released from the funnel 208. The tube 211 may have a pill tube hole ("pill tube hole" or "pill receiving hole") 243 at a center portion of the tube such that when the pill tube hole 243 is facing upwards, indicated by arrow 265, the pill tube hole 243 is substantially aligned with the bottom of the funnel 208. Thus, the pill tube 211 may hold within it a pill (not shown) caught from the funnel until the pill is released out of the medication dispenser. When the system is actuated to release a pill, the pill tube 211 and the pill tube holder 241 may rotate, as indicated by arrows 242, such that the pill tube hole 243 faces downwards and releases the pill from within the hollow pill tube 211 into, for example, an exit tube (as shown in FIG. 1A). The pill dispensing system may accommodate various types of medications by providing a plurality of pill tubes 211 having different sizes and shapes of pill tube holes 243. Again, as an example, a user may scan a prescription bottle or paper prescription (as will be described further when referring to FIGS. 7A-7B), and the medication management platform may inform the user which pill tube 211 should be used for the type of medication that was prescribed, such that the size and shape of the pill tube hole 243 matches the size and shape of the medication or pill. The appropriate pill tube 211 may then be selected, from a variety of provided pill tubes, and inserted into the pill dispensing system.

The pill tube holder 241 may be provided with a first end 261-a and a second end 261-b. The tube holder 241 may be provided with a gear ("gear or gear wheel") 244 at the first end and at the second end. The gears 244 may rotate and cause a rotation of the inner pill tube 211, for example. The pill tube holder 241 may be shaped similar to a half-cylinder, or may have any curved or similarly suitable shape for receiving and holding the pill tube 211, such that the pill tube 211 rests on the holder 241 and such that the pill tube 211 and the pill tube holder 241 rotate together when the pill dispensing system is actuated and turned. The pill tube 211 may be provided with a groove, or channel 250-a along the length of the tube, and the pill tube holder 241 may be provided with a fin 250-b along the length of the pill tube holder. The pill tube holder 241 may be associated and locked together by aligning the groove 250-a with the fin 250-b such that the fin 250-b is captured within the groove. Thus, a movement of the tube holder 241 caused by a rotation of the gears 244 may also cause a movement of the tube 211.

Furthermore, the pill tube 211 may slide into the tube holder 241, while the channel 250-a may be configured to restrict a side-to-side movement of the pill tube 211 within the pill tube holder 241. The pill tube may also be removable from the pill tube holder by sliding the tube in a lengthwise direction away from the tube holder, as indicated by arrow 264.

Figure 3:
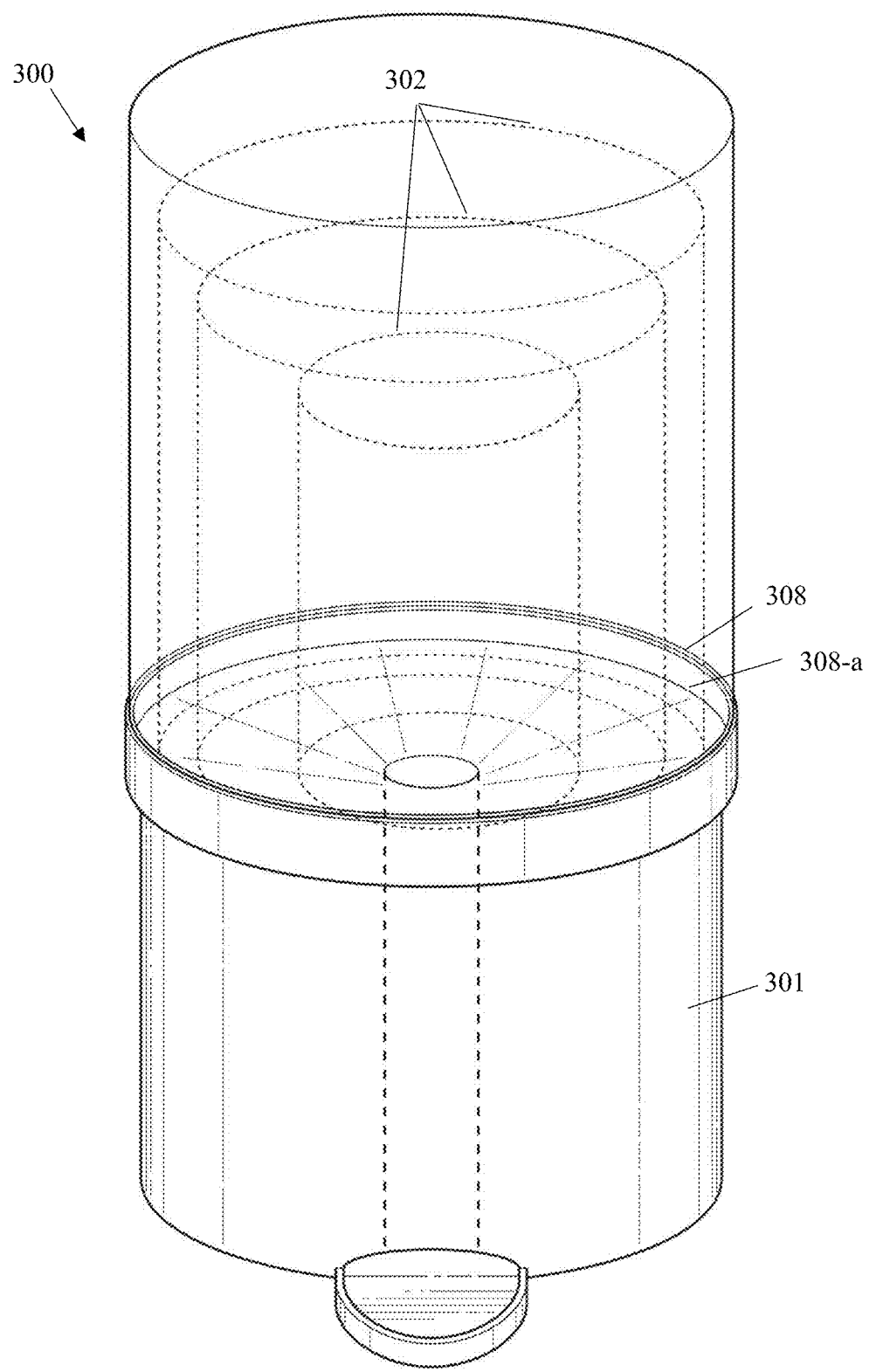
FIG. 3 illustrates front perspective view of another example of the compact dispenser apparatus in an assembled state, according to an aspect.

FIG. 3 illustrates front perspective view of another example of the compact dispenser apparatus 300 in an assembled state, according to an aspect. The compact dispenser 300 may accommodate various sizes of medicine bottles, as shown by the examples indicated by broken lines 302, wherein a bottle as indicated by 302 may screw into the base 301 via the funnel 308. Again, the funnel 308 may be provided with threads 308-*a* such that a bottle can be screwed in, or may be provided with channels for the bottle to slip into, or may be free of any threads. As another example, the funnel 308 may also be provided with channels such that the rim of a bottle 302 may sit within the channels and thus be secured into the funnel 308.

Figure 4:
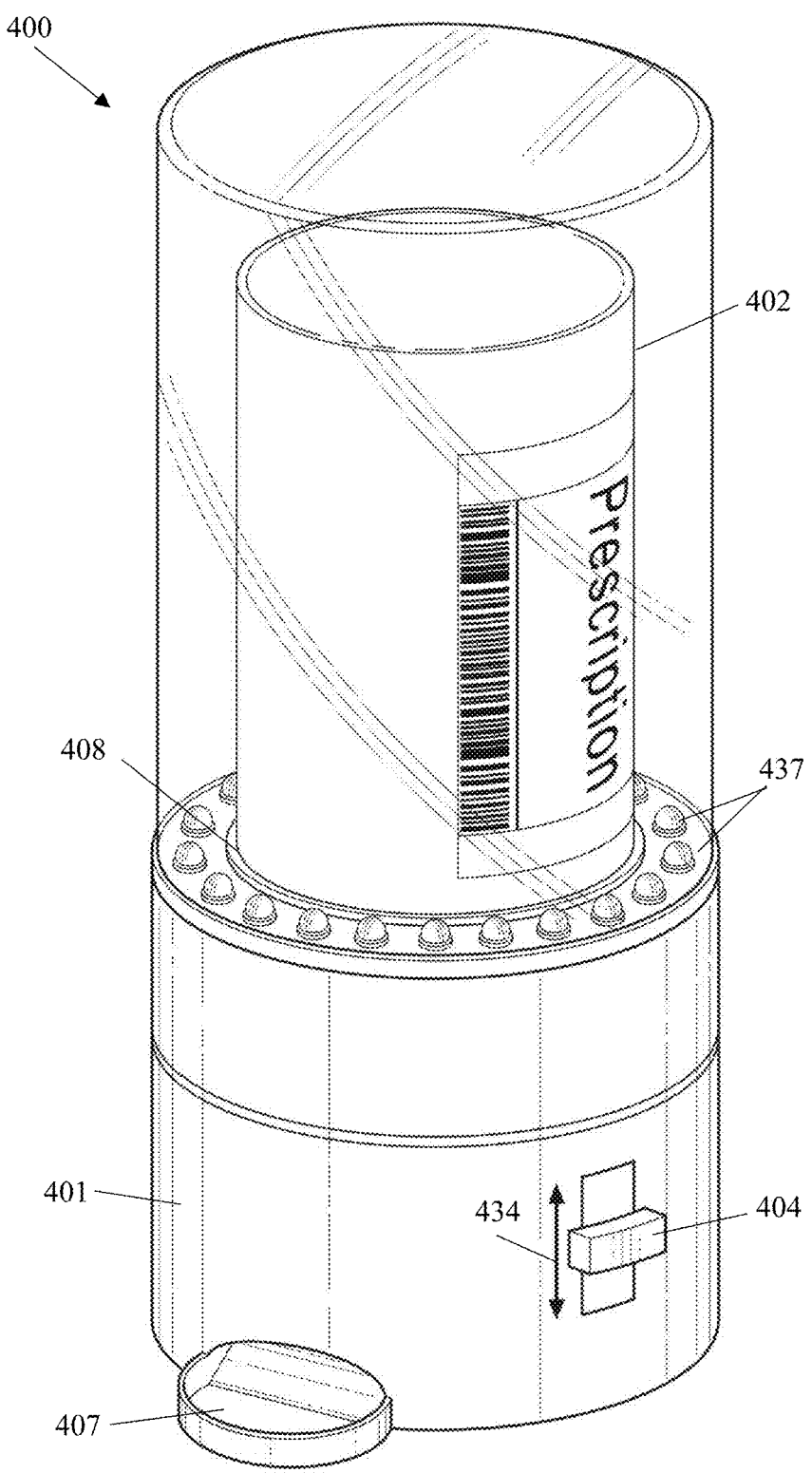
FIG. 4 illustrates the front perspective view of the compact dispenser apparatus in an assembled state, according to an aspect.

FIG. 4 illustrates the front perspective view of the compact dispenser apparatus 400 in an assembled state, according to an aspect. A bottle 402 is also shown attached to the funnel 408 within the base 401. Again, the base 401 may be provided with a lever 404, a pill catcher 407, and may also be provided with lights 437, which may be LED lights, for example. The lever 404 may, again, move in the directions indicated by arrows 434, which may actuate a rack and pinion system.

Figure 5A:
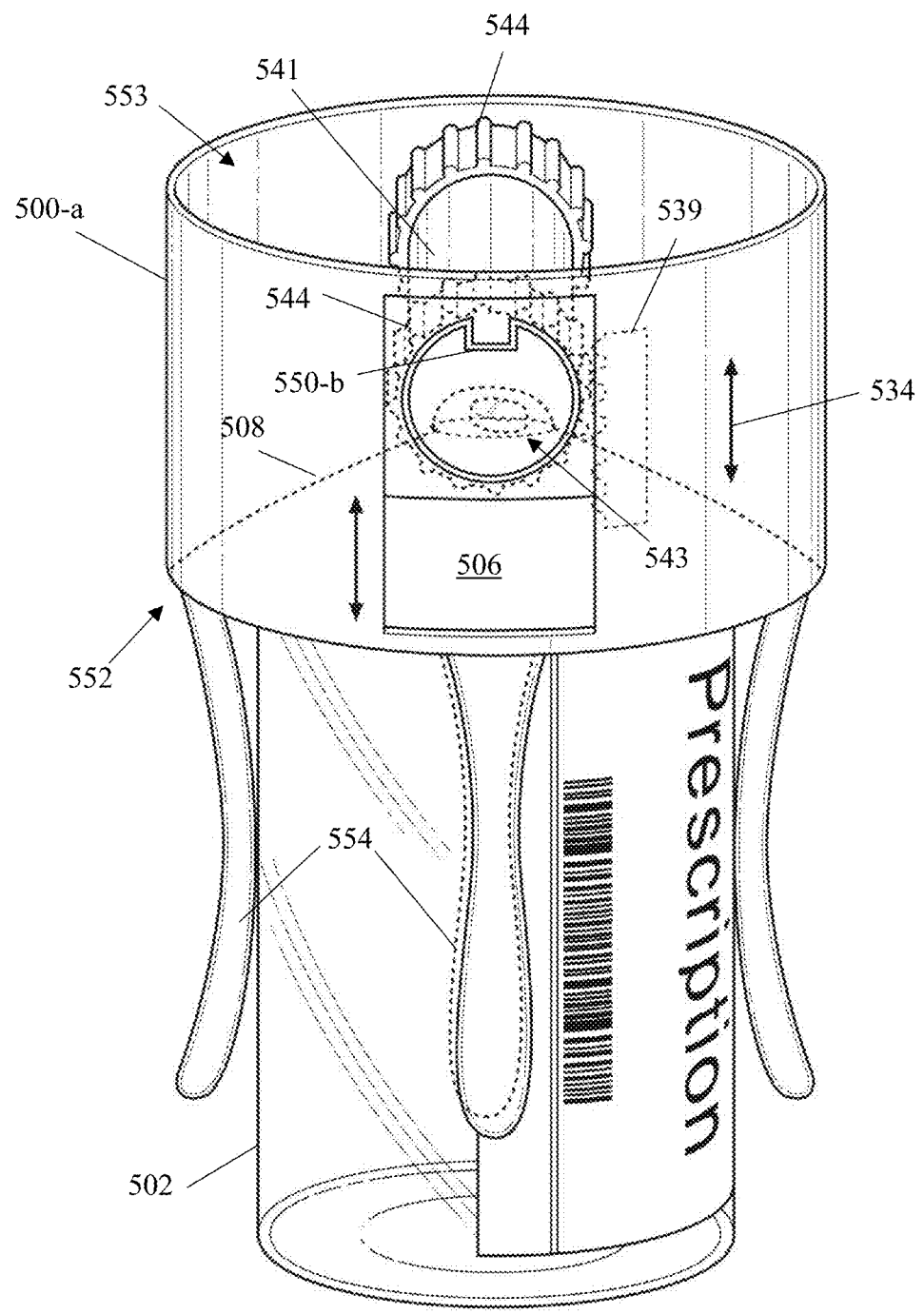
FIGS. 5A-5B illustrate the upside down right perspective view and the right side up left perspective view, respectively, of an open-ended locking pill bottle cap, according to an aspect.
Figure 5B:
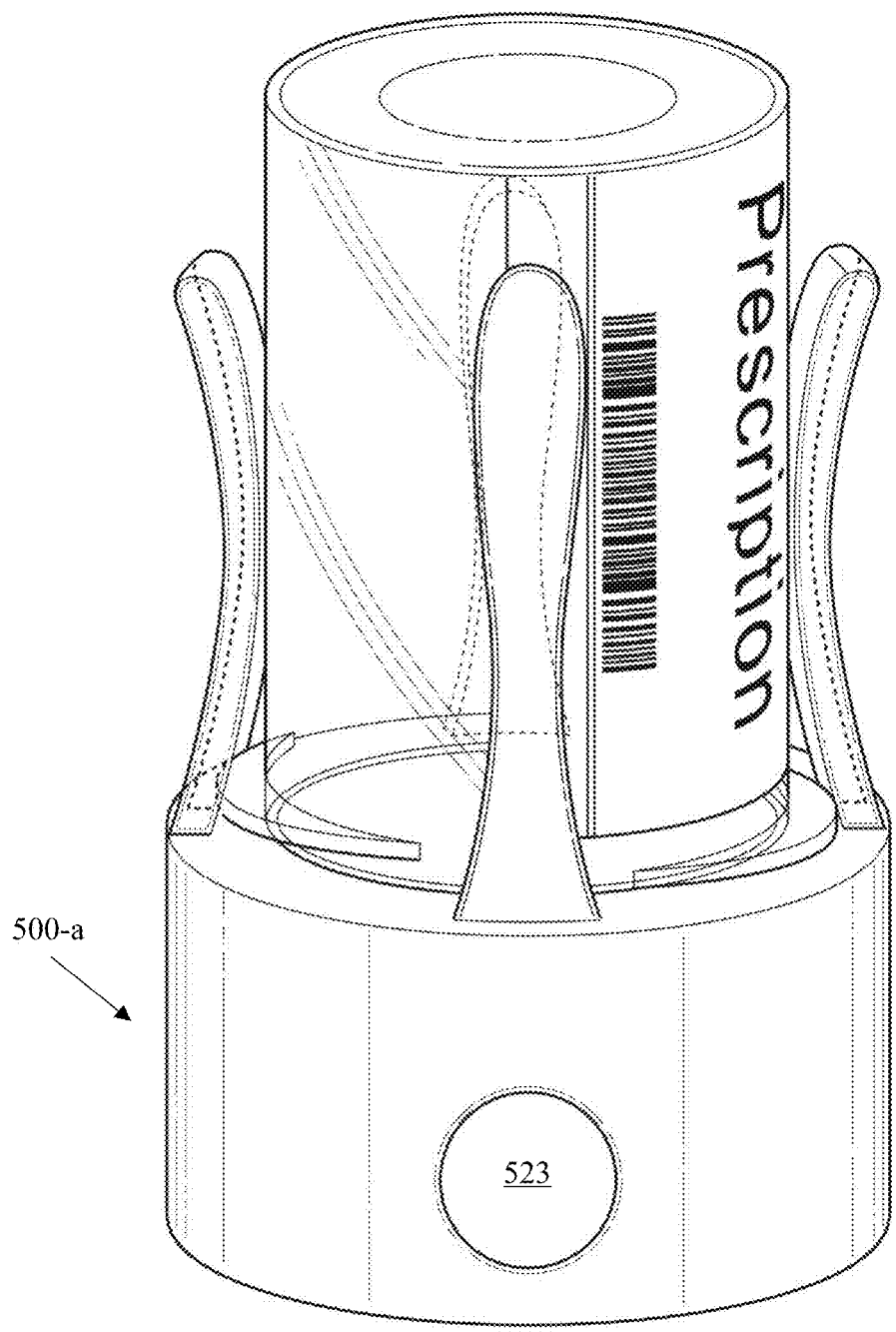

FIGS. 5A-5B illustrate the upside down right perspective view and the right side up left perspective view, respectively, of an open-ended locking pill bottle cap ("open-ended cap," "locking pill bottle cap," "pill bottle cap," "locking cap," or "cap") 500-*a*, according to an aspect. As an example, a pill dispensing system as described when referring to FIGS. 2A-2B may be provided within a cap 500-*a* having a first end 552 for receiving a bottle 502, and an opposite second end 553.

As an example, the cap 500-*a* may house a pill tube holder 541, a pill tube 511, which may be selected according to the size and shape of the medication being used, a funnel 508, a pill receiving hole 543, a fin 550-*b*, gears 544, a gear arm 539, a sliding door 506 on a first side as shown in FIG. 5A, and a release button 523 on a second side opposite to the first side as shown in FIG. 5B.

The gears 544 and a gear arm 539 may be a rack and pinion actuator for actuation of the pill dispensing system, such that the gear arm 539 is a rack of the rack and pinion actuator and the gear 544 is a pinion of the rack and pinion actuator. For example, the rack 539 may be configured to move the pinion 544, thus causing the rotational movement of the tube holder because, for example, the tube holder may be provided with the gear wheel 544.

The second end 553 may be open and may thus provide access to the pill dispensing system, such that an external device or apparatus may access the gear arm 539 in order to provide an actuation of the pill dispensing system. A device, such as a tabletop medication dispenser (as will be further discussed when referring to FIGS. 7A-7C), may provide a means of actuating the gear arm, for example, and may move the gear arm such as in the directions indicated by arrow 534. As also discussed below when referring to FIGS. 7A-18, the cap 500-*a* may be enhanced such that to communicate a mobile application.

The cap 500-*a* may be provided with a means for securing the cap 500-*a* to the bottle 502, such as the vertical arms 554 in the example shown in FIGS. 5A-5B. The vertical arms 554 may be spring-loaded, or may be biased towards each other by any suitable means such that when fitted onto a bottle 502, the arms 554 are able to grip the bottle 502.

Figure 6A:
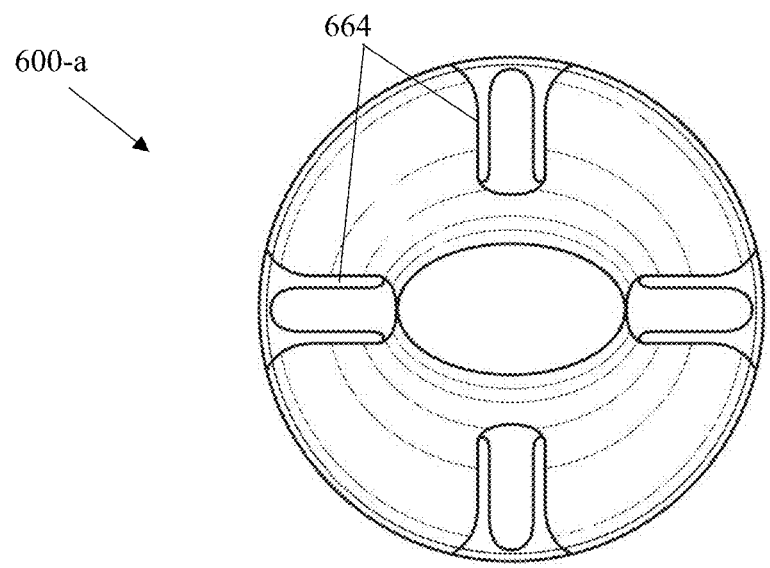
FIGS. 6A-6D illustrate the top plan views of various examples of a locking pill bottle cap, according to an aspect.
Figure 6B:
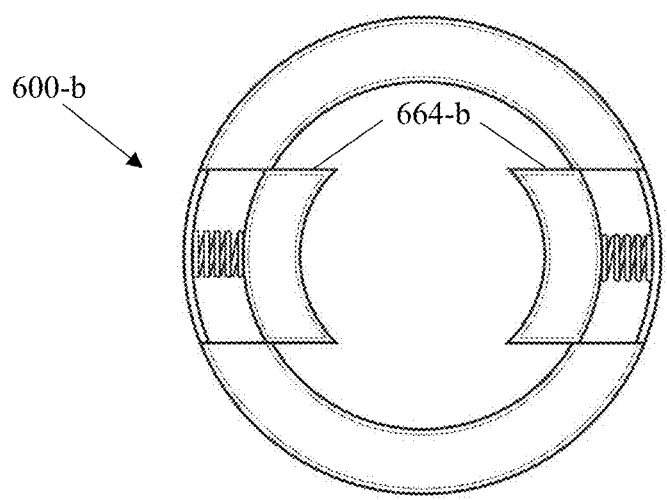
Figure 6C:
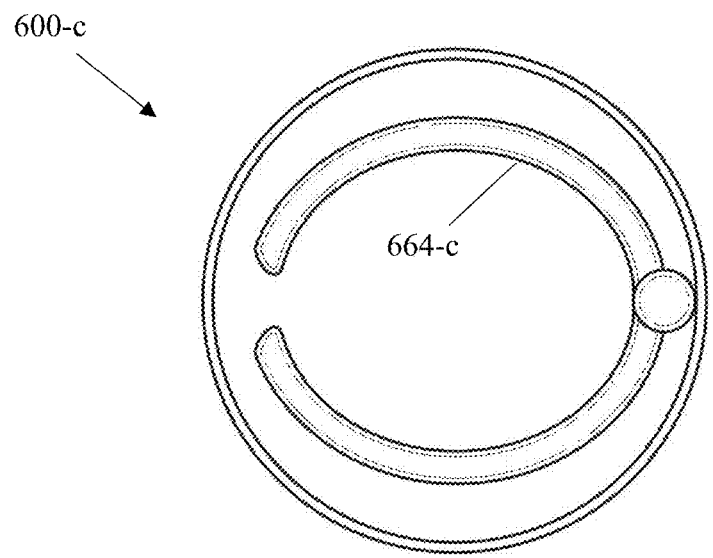
Figure 6D:
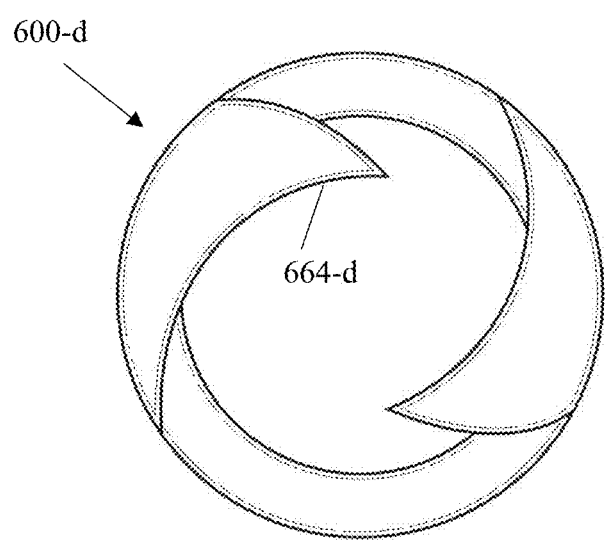

FIGS. 6A-6D illustrate the top plan views of various examples of a locking pill bottle cap 600-*a* through 600-*d*, according to an aspect. The cap 600-*a* of FIG. 6A shows a cap with vertical arms 664, as shown in FIGS. 5A-5B, wherein the vertical arms 664 may grip onto the sides of a bottle. The cap 600-*b* of FIG. 6B shows a cap with spring-loaded grips 664-*b*, which may be biased together. The spring-loaded grips 664-*b* may be pushed apart to be fitted onto a bottle, and when released may bias together to grip onto the bottle. The cap 600-*c* of FIG. 6C shows a clasp 664-*c* which may be biased together, and pushed apart to be fitted onto a bottle. The clasp 664-*c* may be biased together to grip onto the bottle when released. The cap 600-*d* of FIG. 6D shows an aperture closure 664-*d* which may be twisted open or closed in order to release or grip a bottle.

It should be understood that a locking cap may also be secured to a medicine bottle by any suitable means, such as by providing threads, magnetic closure, or any other locking or clasping mechanism, for example.

FIGS. 7A-7C illustrate the front perspective view, the front view, and the sectional top view, respectively, of another example of the medication dispensing apparatus ("tabletop medication dispensing apparatus," or "tabletop apparatus") 770, according to an aspect. The tabletop dispenser 770 may, for example, be placed on a table, counter, or any other suitable surface. The tabletop dispenser 770 may be provided with a housing 771, cameras 715 and 772, a screen 714, a control panel 717, a maintenance door 718, a pill loader 719, a dispensing area 716 and a conveyer belt 720. The screen 714 may, for example, be a touchscreen interface. The maintenance door 718 may allow a user access to the inside of the apparatus for maintenance, changing parts, or any other purpose that requires access to the interior of the apparatus. The maintenance door 718 may be opened with, for example, a release button 718-*a*, and may swing outwards such as in a direction indicated by arrow 747. As an example, a camera 715 may be used for making video calls or for recording videos, and a camera 772 may be used for sensing, scanning, or reading prescriptions.

Exemplary additional features that the tabletop dispenser 770 may be provided with may include a speaker, Bluetooth and Wi-Fi connectivity capabilities, a power source or cord for connecting to a power source, BIOS, a maintenance door release button 718-*a*, and a light (not pictured).

As an example, the tabletop dispenser may be used in place of or in conjunction with a mobile application for medication management, and may provide the user with the functions provided by the mobile application. As an example, the camera 772 may scan prescriptions in order to import data, or a smartphone with a camera and the mobile application for medication management may be used to scan prescriptions and import data.

To begin use of the tabletop dispenser 770, a user may carry out the following exemplary process. First, the user touches a button of the control panel 717 or on the touchscreen interface 714 to begin scanning. The command from the control panel or touchscreen activates the built-in device camera 715. Next, the user lines up the camera view with the prescription label. The tabletop dispenser 770 may be provided with OCR or similar technology to read the information on the prescription label and converts the image to text that becomes imported into the database for medication management. The medication management platform can then store the data such as information related to the pharmacy, patient, doctor or other care provider, and medication into the user's profile. Next, the medication management platform instructs the user on the type of cap or pill tube that should be used with the type of medication that was scanned in. Next, the user removes the medication bottle's provided cap, and replaces the cap with the specified cap such that the hole of the pill tube is sized and shaped for the medication being used with the tabletop dispenser. Next, the user inserts the medication bottle fitted with the specified cap into the tabletop dispenser by opening the pill loader 719 and placing the bottle inside. Next, the medication management platform may provide the user with alerts through the tabletop dispenser, a smartphone application, or both, such that the user is notified when medication needs to be consumed, and the user may press a button on the dispenser to release a pill. Next, the medication management platform connected with the dispenser may turn off the alert, and record the medication consumption event.

The medication management platform may track pill dispensing, and alert the user whenever a pill is dispensed. An advantage may be that the user may not need to track or record medication consumption themselves, and any unauthorized dispensing of pills may also be alerted to the user. Another advantage may be that the user may have access to medical history, medical benefits, side effects, and other information about a medication such as active ingredients and interactions with other medication. Doctors may also have the ability to set up a medication reconciliation profile for a user, and may make or track changes to the user's profile. The user may also have the option of setting up family alerts, social support, and face-to-face calls with doctors, the doctor's office, and family members, for example. As an example, a plurality of cameras may be provided, such as a camera 772 for scanning a prescription, and a camera 715 for making video calls or making videos when dispensing medication.

The user may also have access to lists of medication, medication schedule or timetables, alerts, doctors, education about medicine, warnings, and social support through the medication management platform accessed through the tabletop dispenser 770 or through a mobile application.

As shown in FIG. 7C, the interior of the tabletop dispenser 770 may be provided with a conveyer belt 720, such that multiple medicine bottles 702 may be stored in the dispenser 770 and dispensed according to a user's needs or prescription. Each medicine bottle 702 inserted into the tabletop dispenser 770 may be fitted with an appropriate open-ended cap such as the caps shown in FIGS. 5A-6D, where an actuator from the tabletop dispenser 770 may reach into the pill dispensing system of the cap and actuate the pill dispensing. The tabletop dispenser 770 may, for example, dispense pills using a system similar to the pill dispensing system as shown and described in FIGS. 1A-1B. The pills may then dispense into the dispensing area 716, which may be provided with a light (not pictured) for the user to easily see and access the medication.

Again, the medication management platform may be used with a tabletop dispenser 770, which may display information to the user on the screen 714, and the platform may also be used with a mobile application, which may utilize a smartphone or similar device to display information to the user. The user may also use both the tabletop dispenser 770 and a mobile application to track and manage their medication with the medication management platform, and the platform may provide syncing capabilities such that both the dispenser 770 and the mobile device are in communication and updated, for example.

Figure 8A:
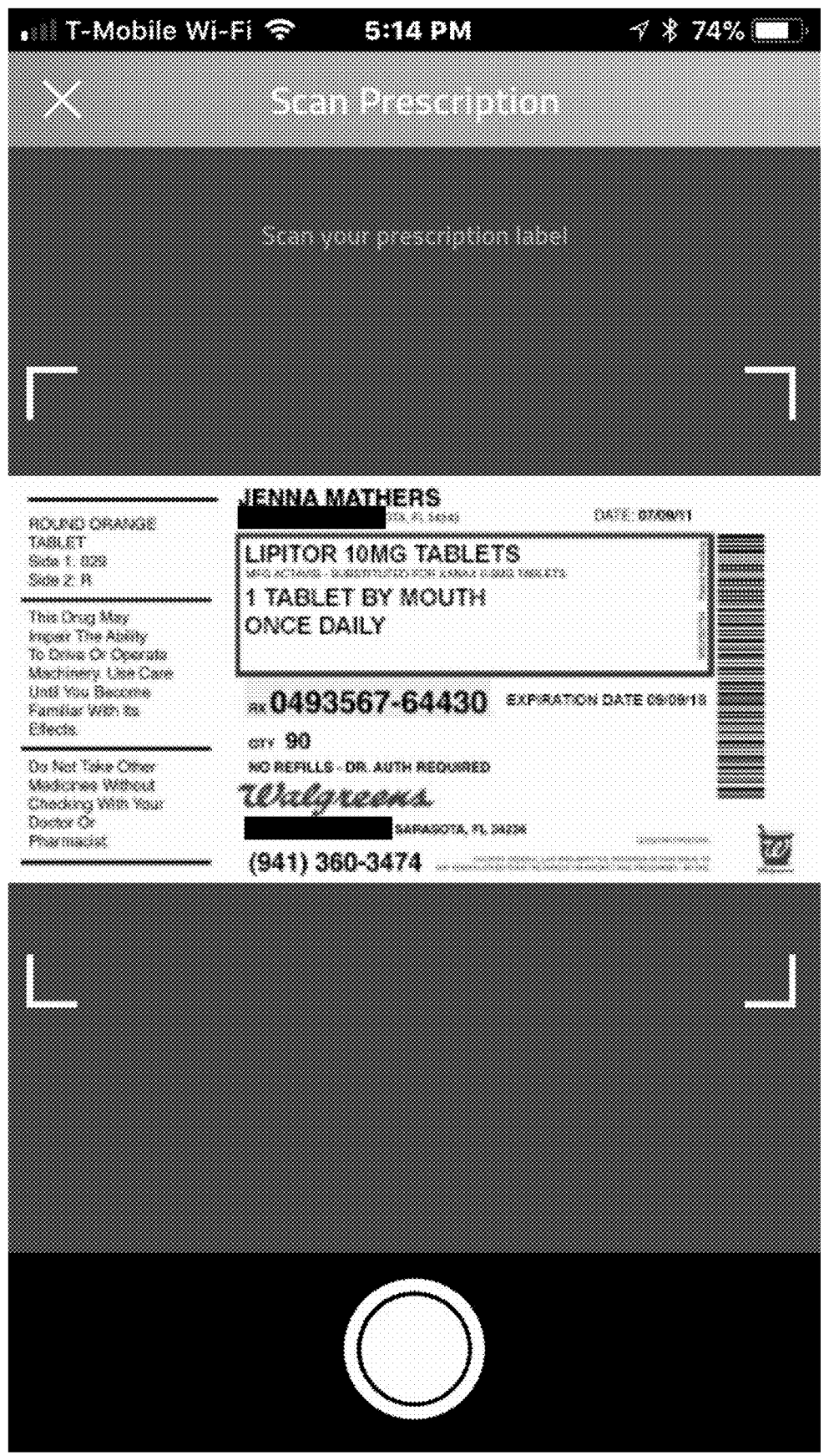
FIGS. 8A-8C illustrates examples of a user interface that may be accessed by a user to scan a prescription and import the information contained within it into the medication management platform, according to an aspect.
Figure 8B:
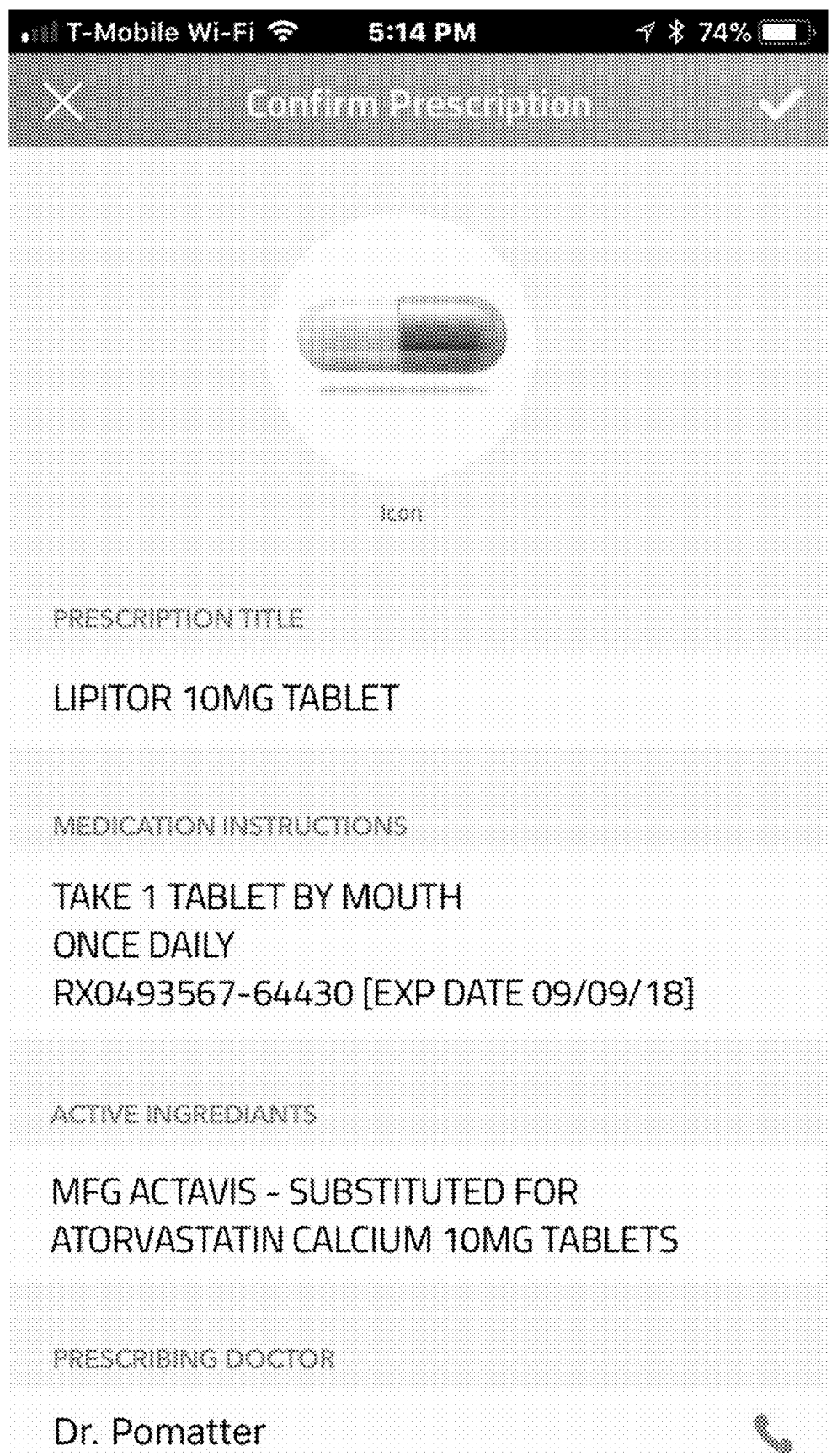
Figure 8C:
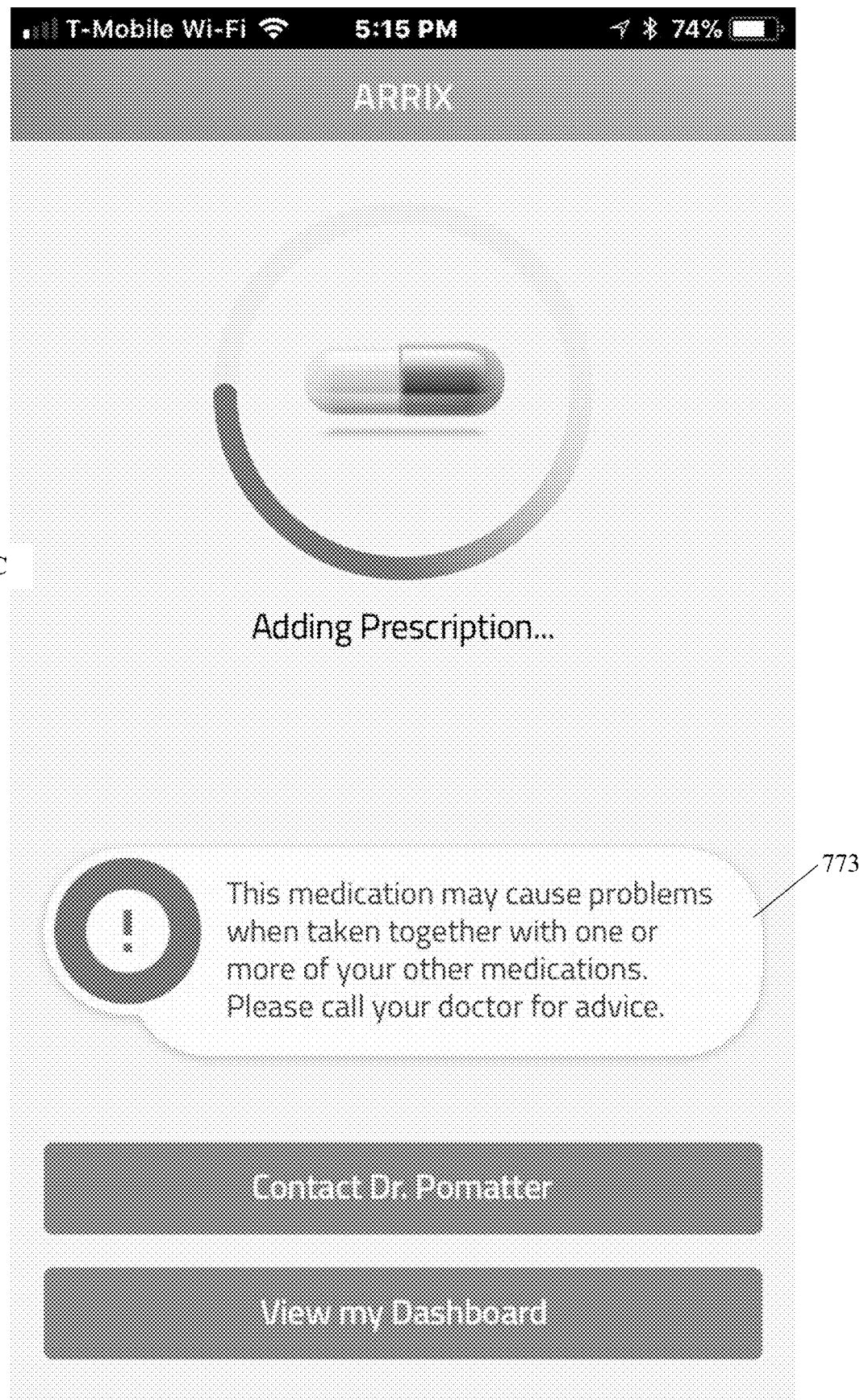

FIGS. 8A-8C illustrates examples of a user interface that may be accessed by a user to scan a prescription and import the information contained within it into the medication management platform, according to an aspect. It should be understood that while the focus of FIGS. 8A-12C is on accessing the medication management platform through a mobile application, similar interfaces may be accessed and provided to the user if accessing the medication management platform through the tabletop dispenser as shown in FIGS. 7A-7C, or through a web browser such as on a computer or other electronic device.

An exemplary process for using the medication management platform is as follows. First, the user downloads and installs the medication management platform as a mobile application onto their electronic device, or accesses the platform through a computer, or may access the medication management platform provided with a tabletop apparatus (as shown by 770 in FIGS. 7A-7C). Next, the user picks up medication from a pharmacy and makes note of whether or not a paper prescription is included with the medication. Next, the user launches the application on their electronic device or tabletop dispenser. Next, the user launches the camera of the mobile device or tabletop dispenser through the application, such as by pressing an animated scan button. As an example, scanning may also be prompted by inserted a prescription into area 716, when the camera senses a readable prescription. Next, the user lines up the camera to capture an image of the prescription medication label. Next, the OCR technology of the medication management platform converts the image into text, and imports the data into the user's profile and the platform database. The medication management platform may then display relevant information to the user such as instructions, and provide the user with timed notifications and alerts related to the medication and the prescription schedule.

As shown in FIGS. 8B-8C, various confirmation screens may be shown to a user when adding a prescription, as an example. After scanning a prescription, information about the medication and the doctor's information may be displayed to the user, as shown in FIG. 8B. The information may also be accessed through the application by the user later on when accessing the platform. The user may also easily access the ability to contact their doctor through the platform. Warnings or other similar relevant notifications 773 may be displayed to the user when the medication or prescription is added to the database or user's profile.

Figure 9A:
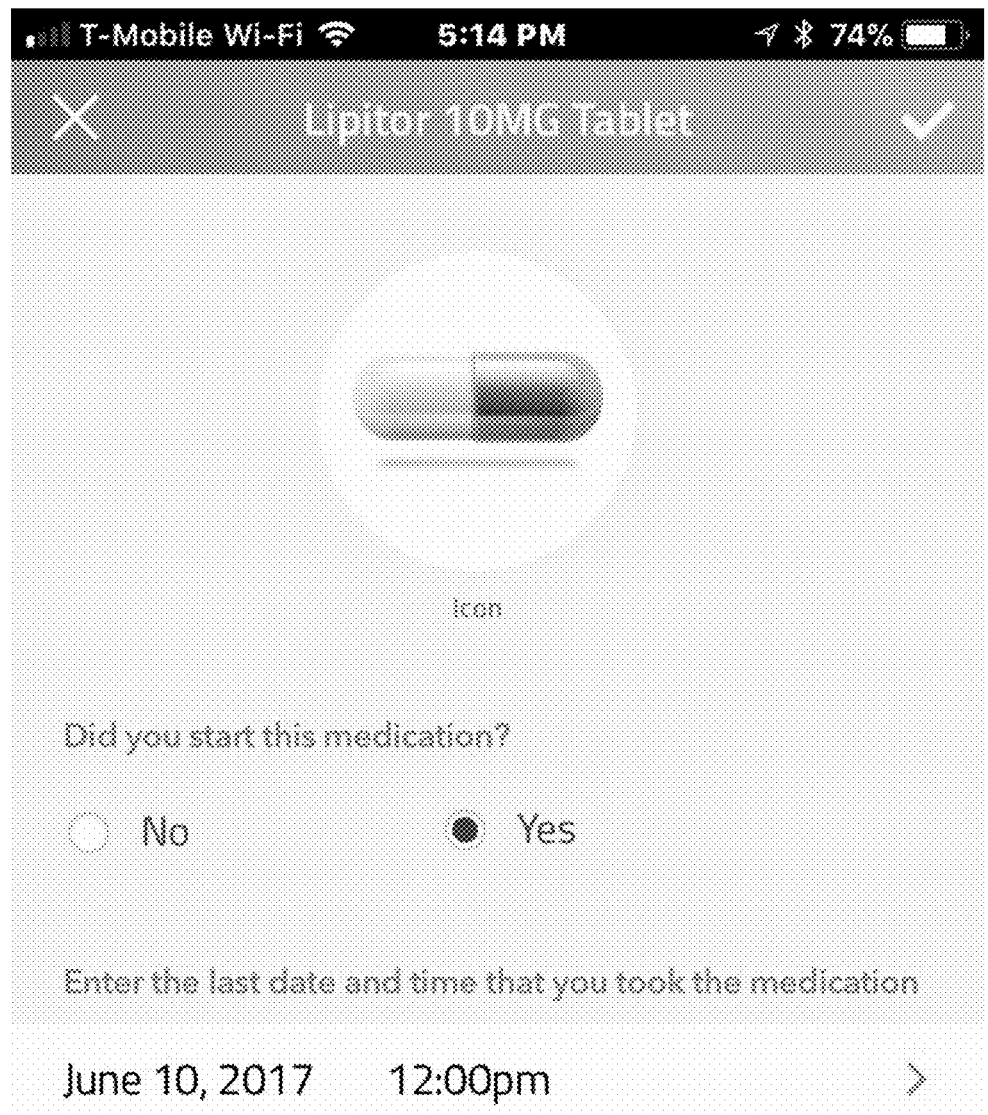
FIGS. 9A-9C show examples of user interfaces that may be accessed by a user to begin a prescription schedule or begin tracking their medication intake using the medication management platform, according to an aspect.
Figure 9B:
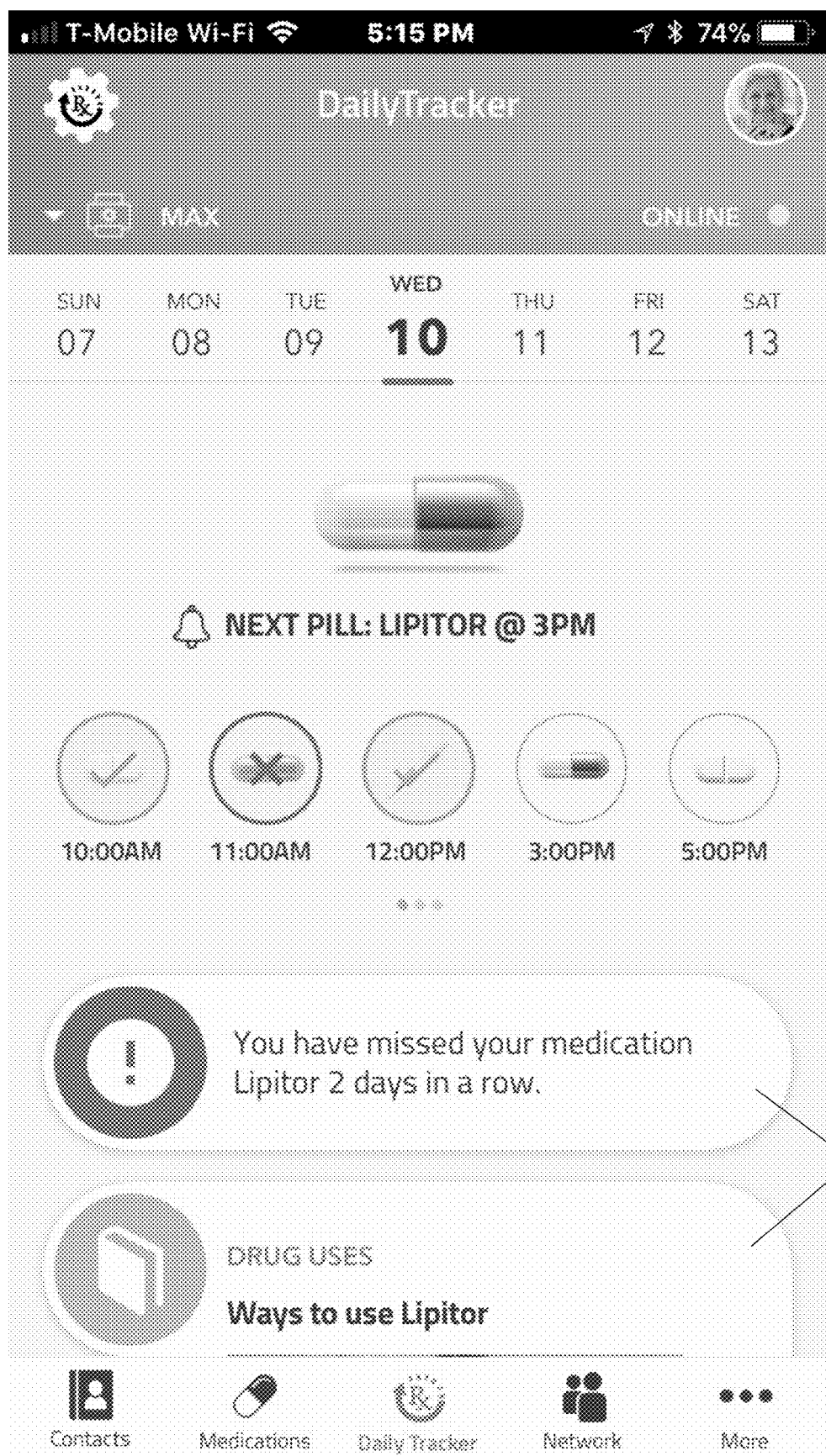
Figure 9C:
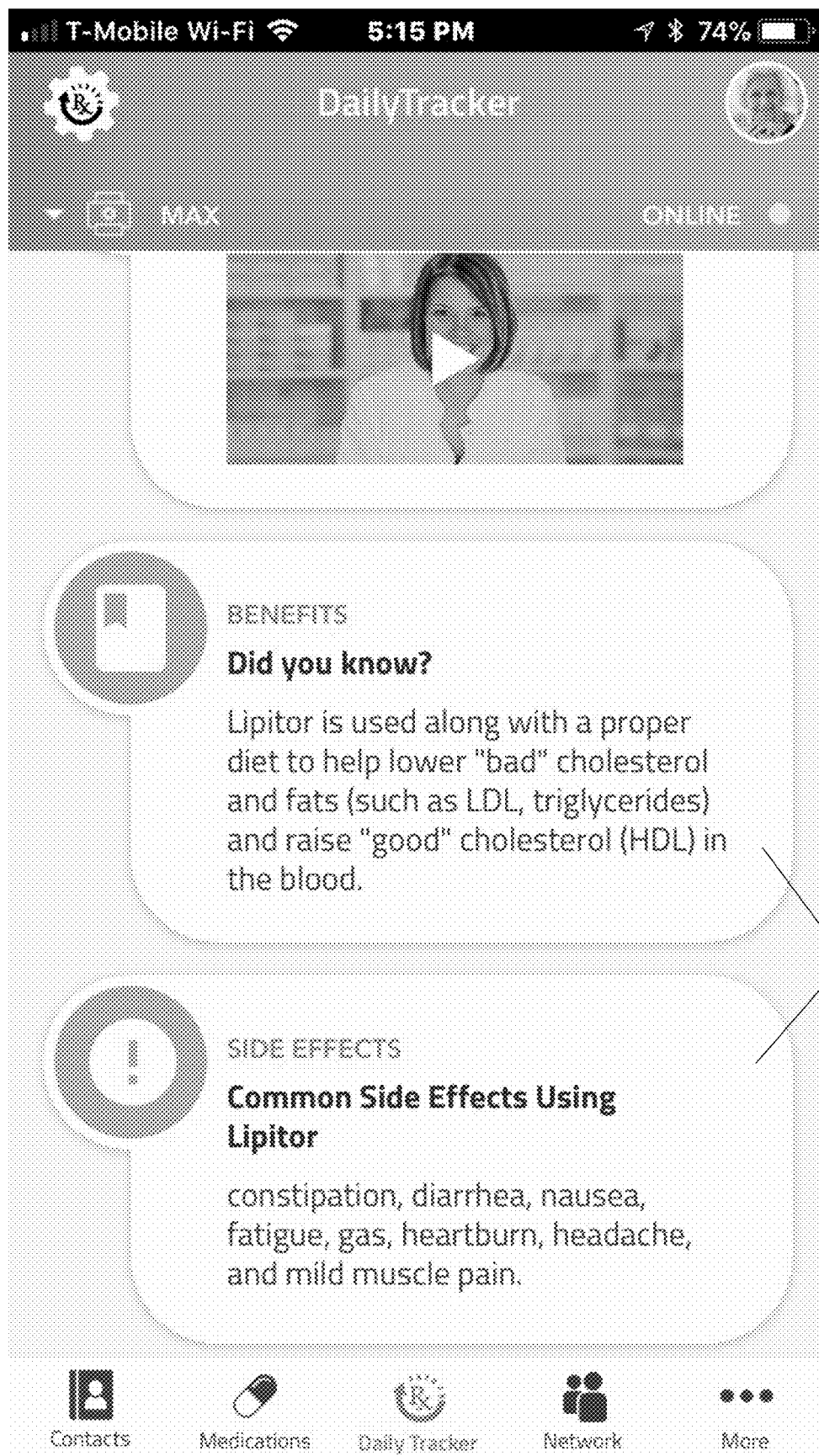

FIGS. 9A-9C show examples of user interfaces that may be accessed by a user to begin a prescription schedule or begin tracking their medication intake using the medication management platform, according to an aspect. Various prompts or questions may be provided to the user such that medication tracking may take place and be recorded by the medication management platform. A calendar may also be provided to the user to view a schedule of medication intake, and information such as the next scheduled doses may be shown to the user, as shown in FIG. 9B. Warnings or notices about a user's prescription medication may be shown, such as the examples 774, as well as additional information such as the examples shown as 775 regarding the medication.

Figure 10A:
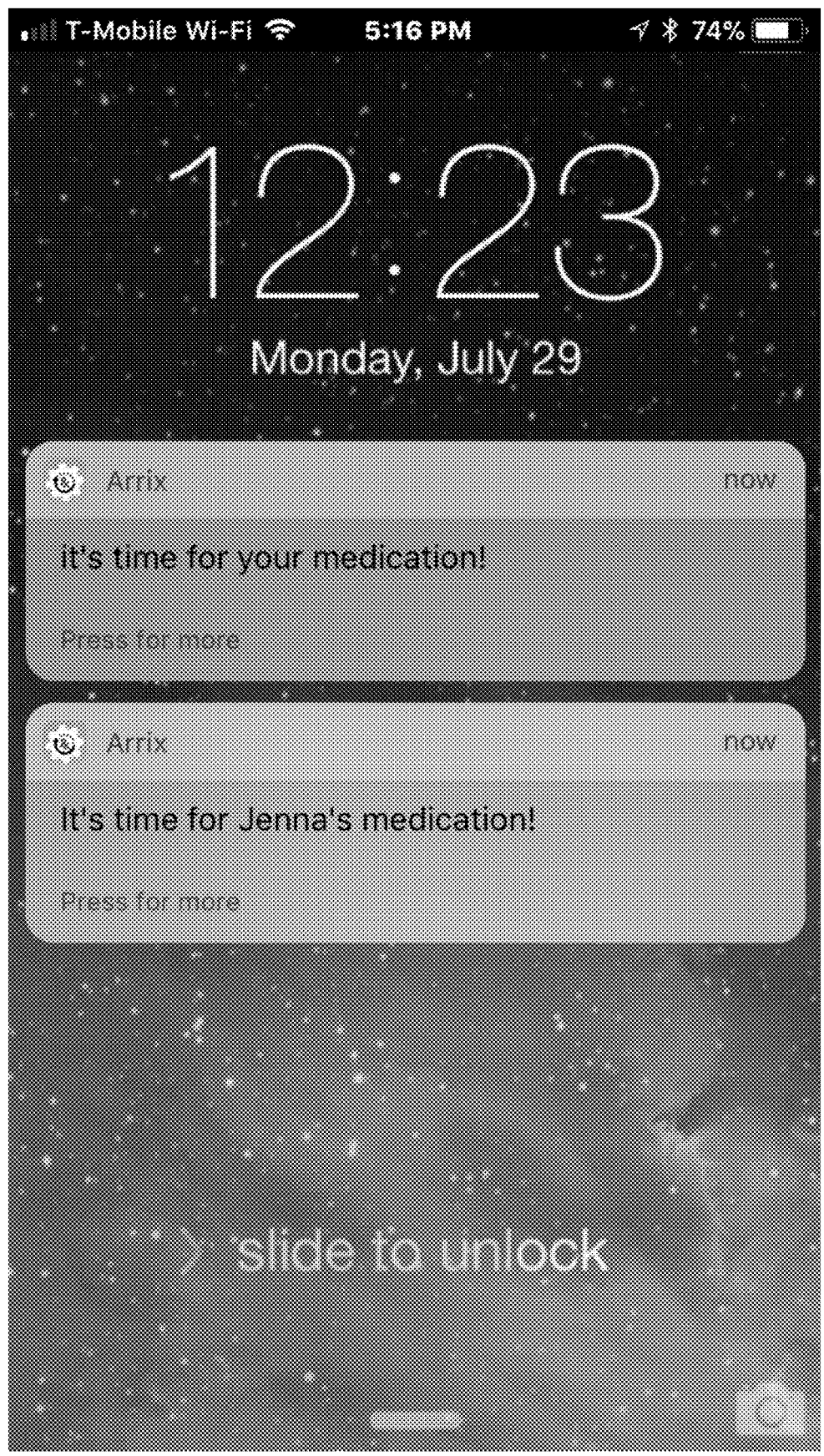
FIGS. 10A-10B show examples of user interface that may be shown to a user related to receiving alerts or notifications about a prescription, according to an aspect.
Figure 10B:
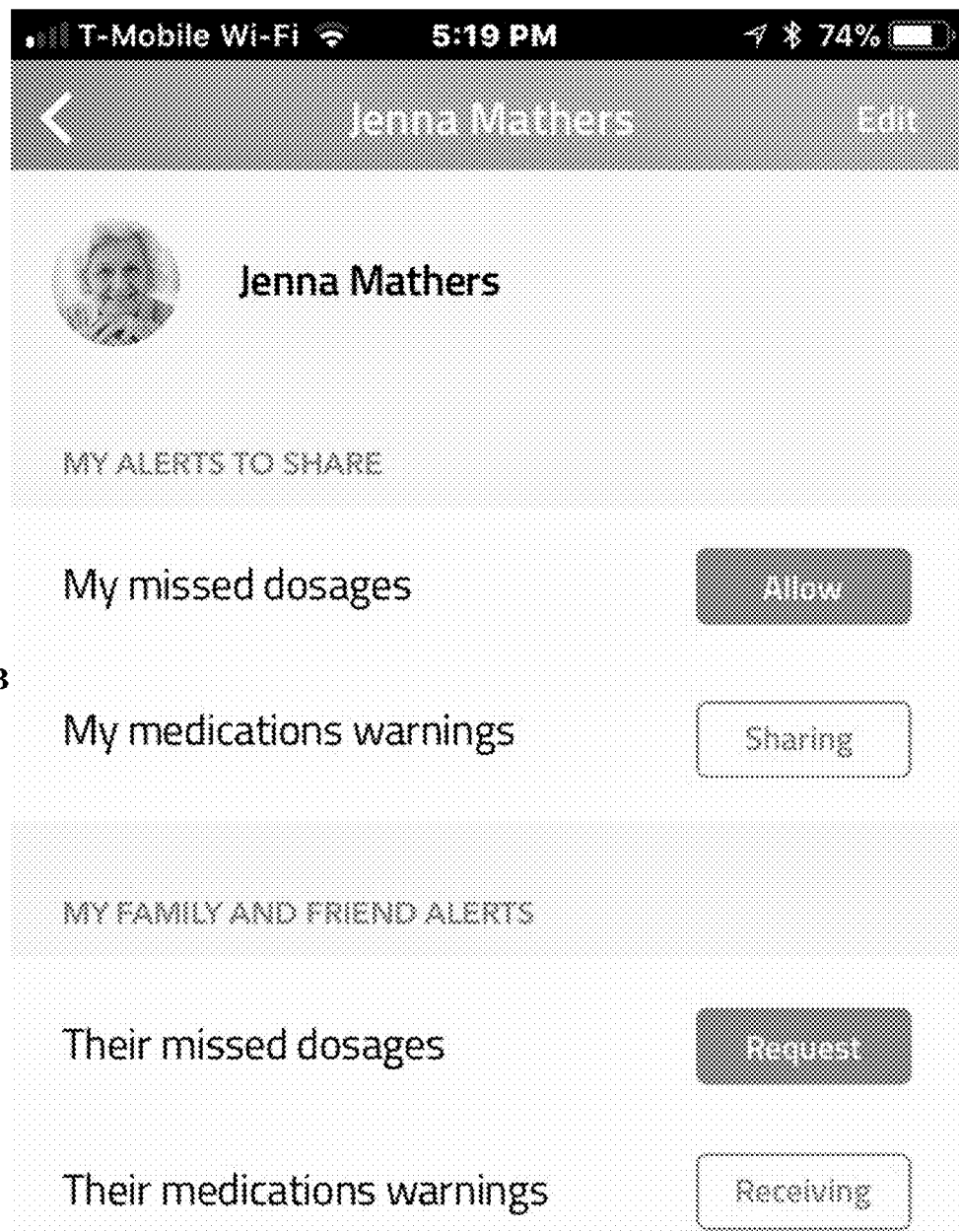

FIGS. 10A-10B show examples of user interface that may be shown to a user related to receiving alerts or notifications about a prescription, according to an aspect. When a user has begun tracking medication intake for a particular prescription, the medication management platform may send notifications such as push notifications on a user's electronic device. A user may also receive alerts for another user's medication schedule, for example, when users wish to support or track another person's prescription schedules. As shown in FIG. 10B, a user may select the types of alerts they wish to receive, such as an alert for missing a dosage or a warning about medications that are stored in their user profile. A user may also opt to receive alerts and notifications related to another user's medication management, for example, as shown in FIG. 10B. Similar notifications may also be sent via colored lights of a compact dispenser as shown in FIGS. 1A-1B, for example, or through the touchscreen interface of a tabletop dispenser as shown in FIGS. 7A-7B.

Figure 11A:
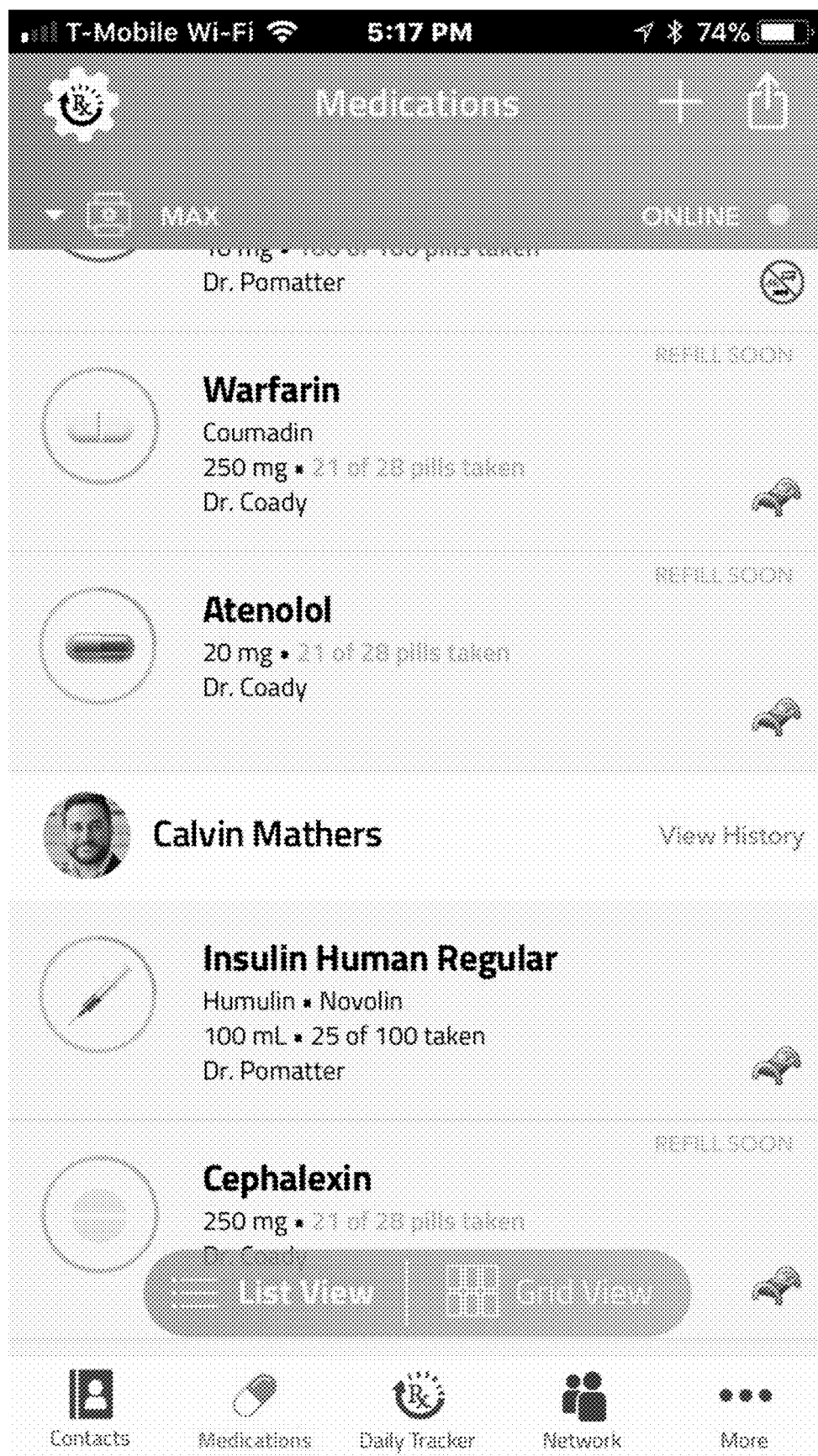
FIGS. 11A-11B show examples of user interfaces having a list view and a grid view, respectively, that may be accessed by a user to view the various prescriptions or medication schedules stored into their profile or another user's profile, according to an aspect.
Figure 11B:
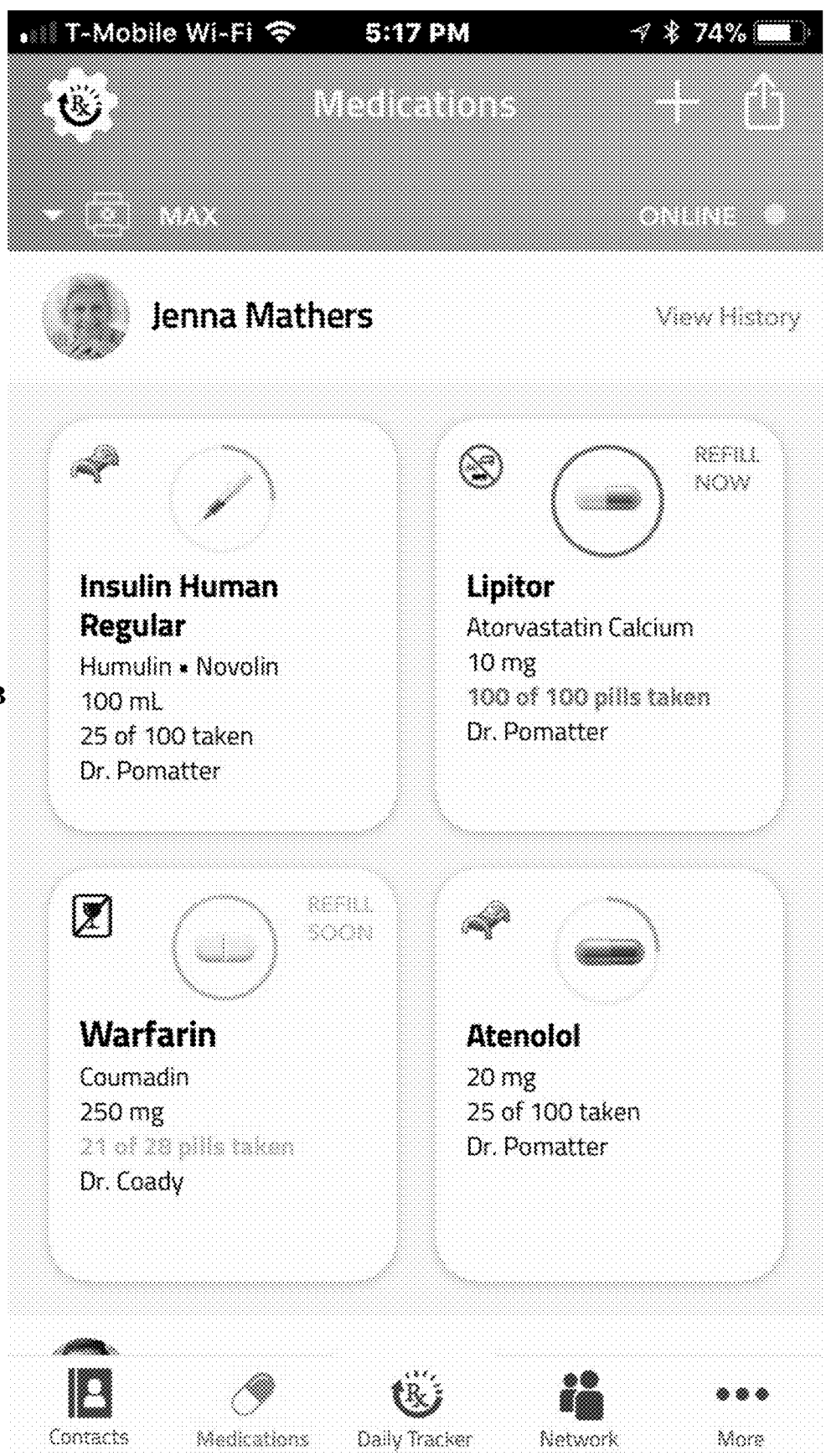

FIGS. 11A-11B show examples of user interfaces having a list view and a grid view, respectively, that may be accessed by a user to view the various prescriptions or medication schedules stored into their profile or another user's profile, according to an aspect. From the list or grid view, a user may select a particular medication or prescription schedule to view further information, as will be discussed when referring to FIGS. 12A-12C.

Figure 12A:
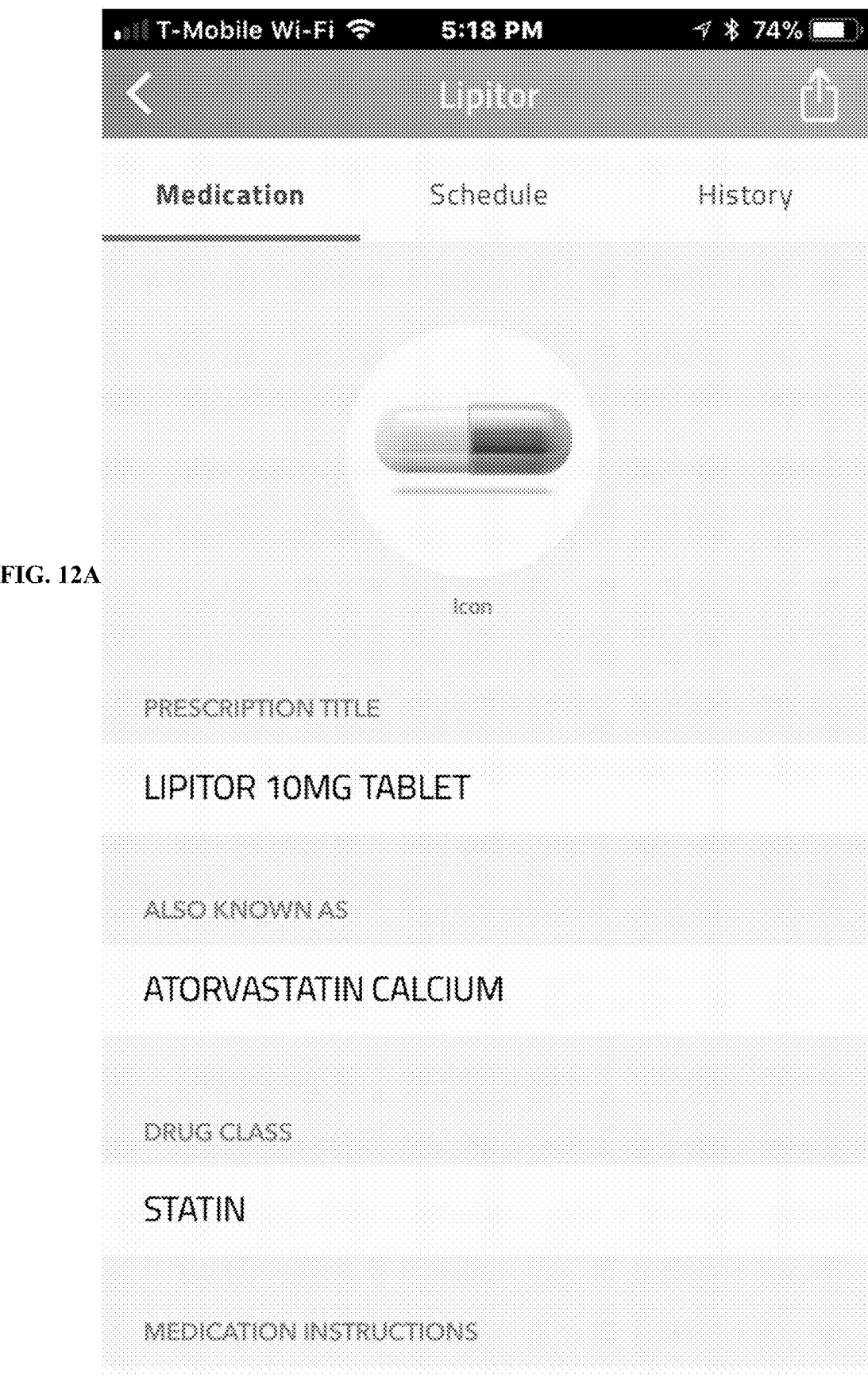
FIGS. 12A-12C show examples of user interfaces that may be accessed by a user when selecting a medication or prescription to view more information about the medication, according to an aspect.
Figure 12B:
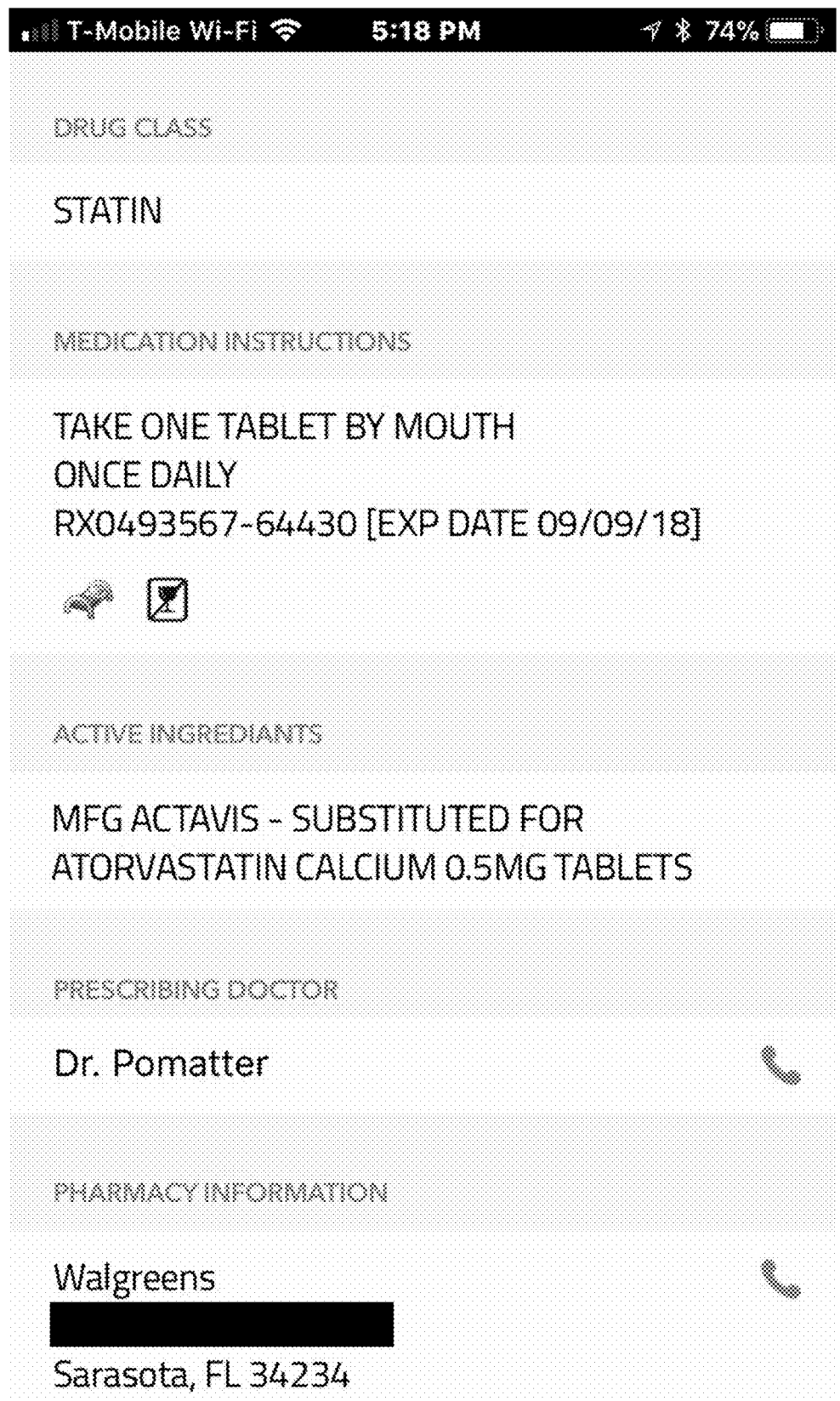
Figure 12C:

FIGS. 12A-12C show examples of user interfaces that may be accessed by a user when selecting a medication or prescription to view more information about the medication, according to an aspect. Exemplary information that may be provided to a user may include the type of medication, drug class, medication instructions, active ingredients, the prescribing doctor, pharmacy information, benefits and uses of the medication, side effects, and links to further reading.

Figure 13:
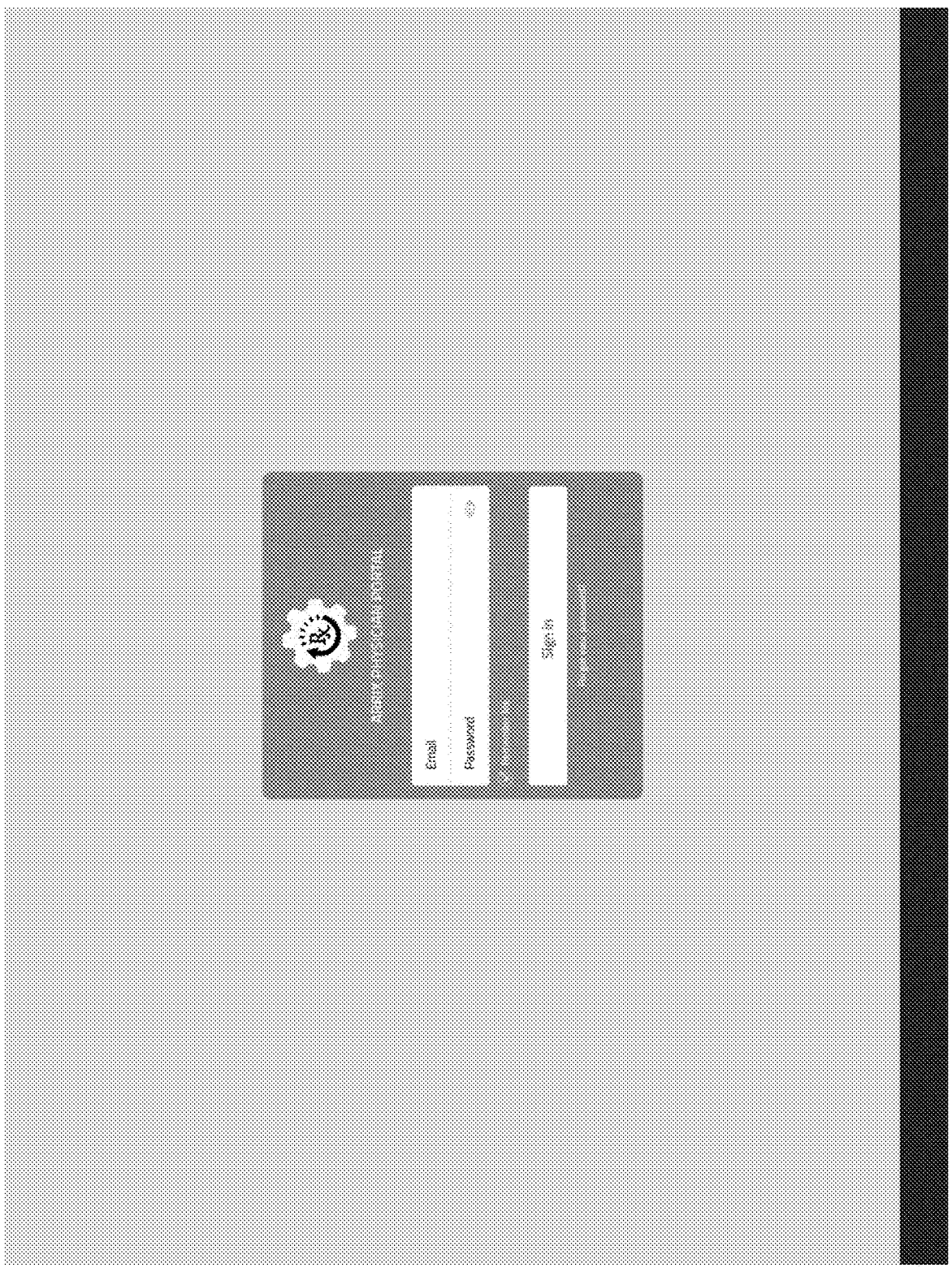
FIG. 13 shows an example of a user interface that may be accessed by a user to utilize a physician's portal of the medication management platform, according to an aspect.
Figure 14:
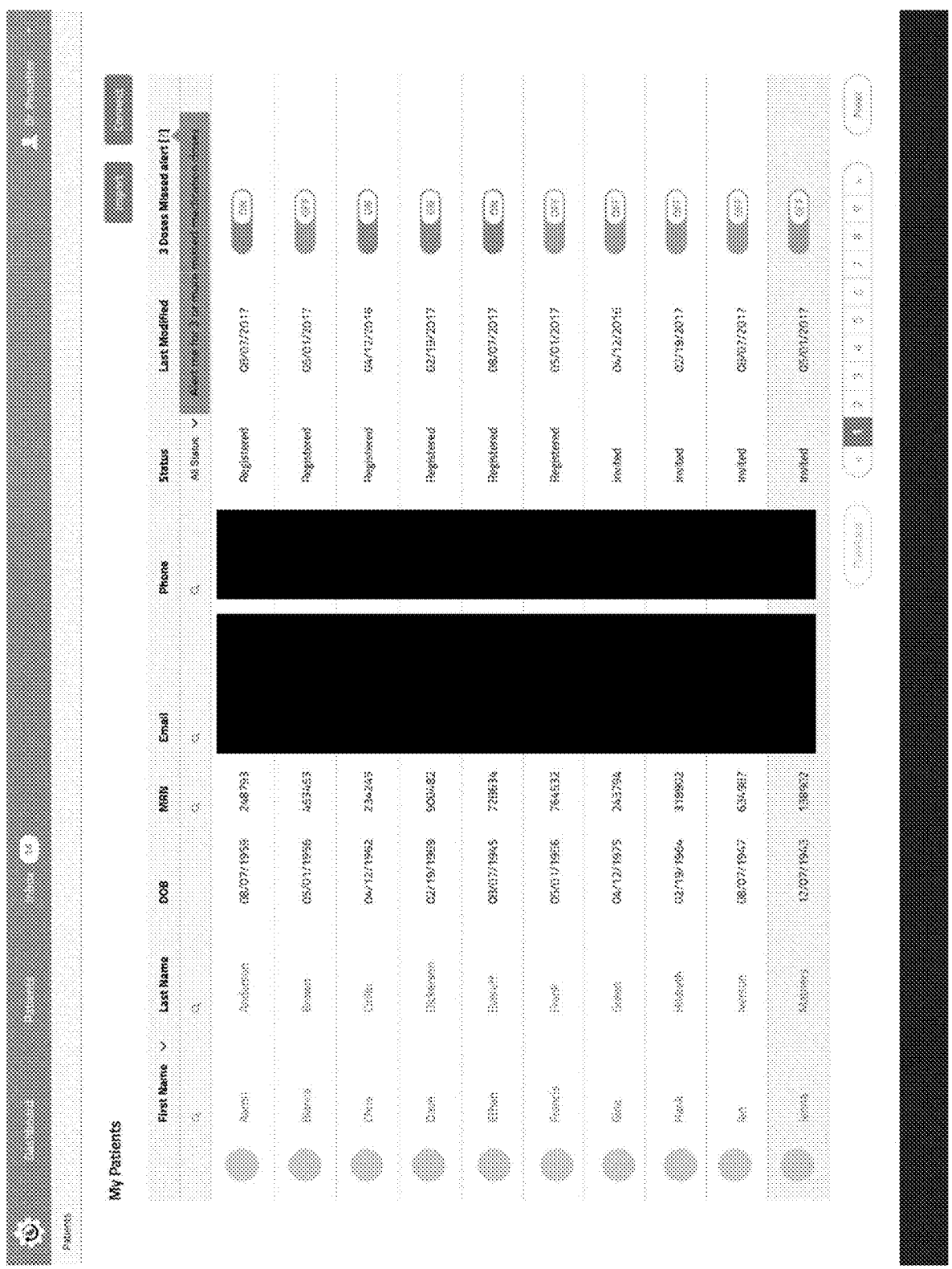
FIG. 14 shows an example of a user interface of a physician's portal of the medication management platform displaying a list of patients under a user's care, according to an aspect.

FIG. 13 shows an example of a user interface that may be accessed by a user to utilize a physician's portal of the medication management platform, according to an aspect. A doctor or physician may use the medication management platform to manage the prescriptions prescribed to their patients, for example. It should be understood that while the focus of FIGS. 13-18 is on accessing a physician's portal of the medication management platform through a web browser of a computer or similar electronic device, similar interfaces may be accessed and provided to the user if accessing the medication management platform through the tabletop dispenser as shown in FIGS. 7A-7C, or through a mobile application FIG. 14 shows an example of a user interface of a physician's portal of the medication management platform displaying a list of patients under a user's care, according to an aspect.

Figure 15A:
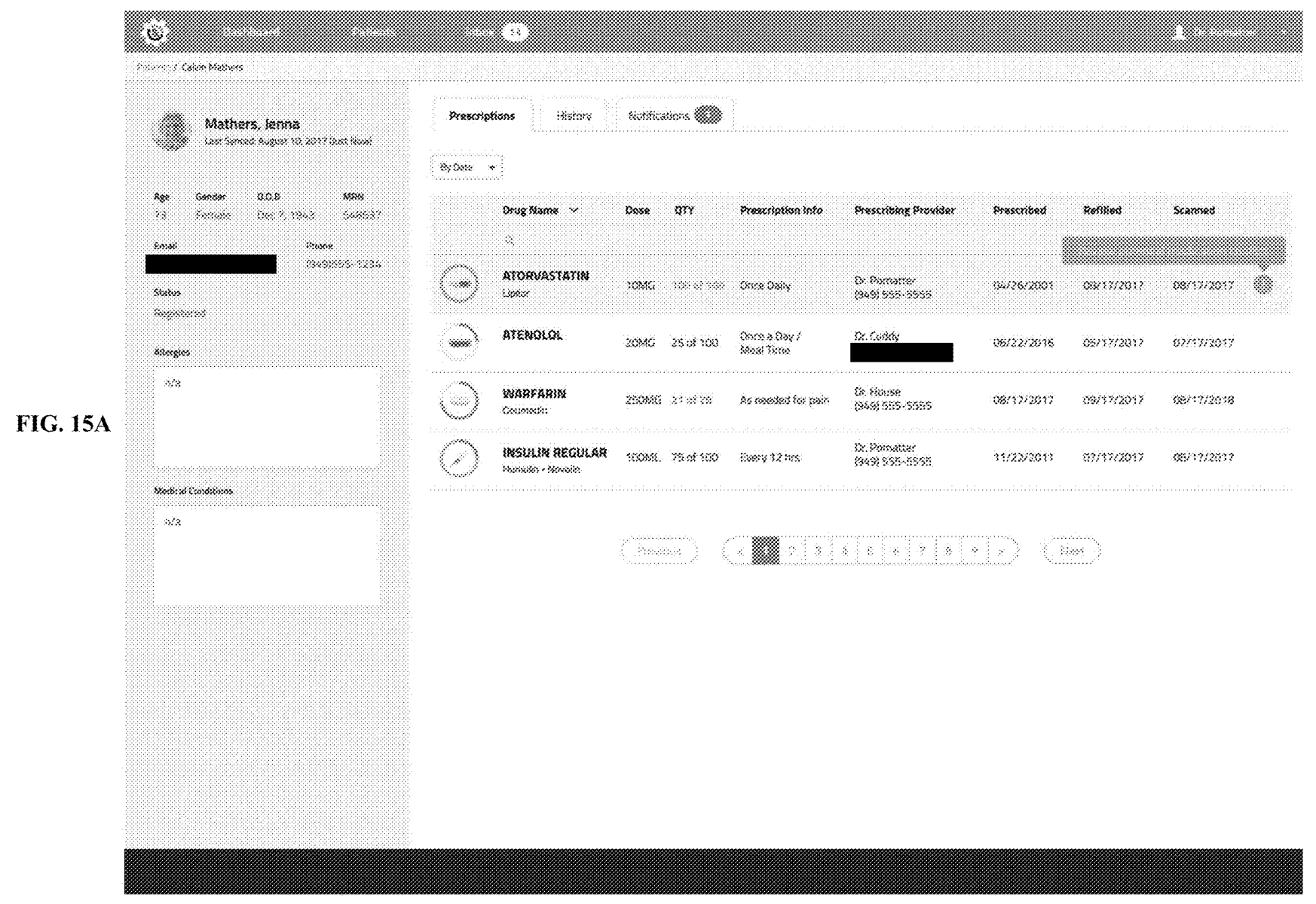
Figure 15B:
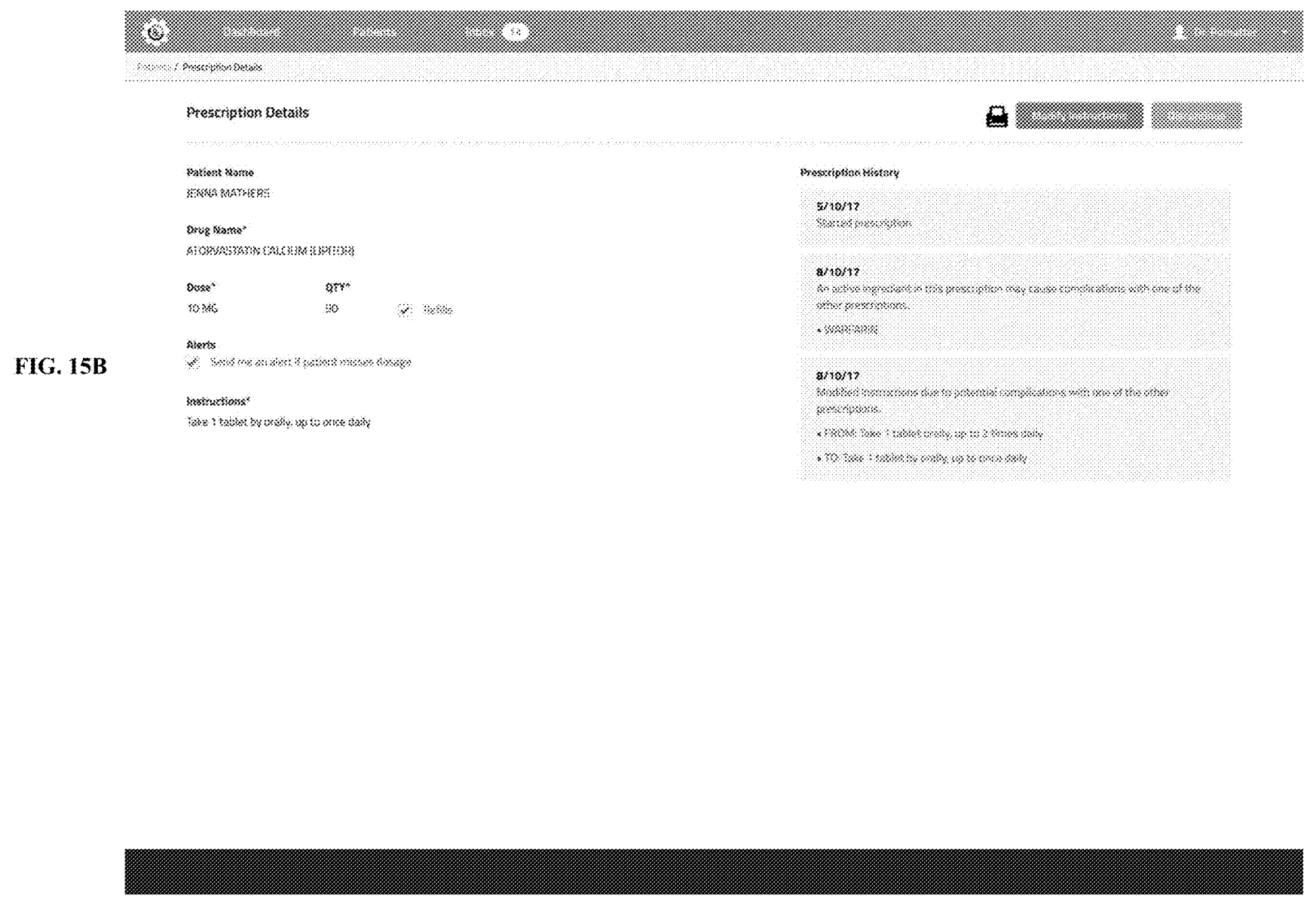

FIGS. 15A-15B show examples of user interfaces of a physician's portal of the medication management platform showing a detailed view of an individual patient under the user's care, according to an aspect.

Figure 16A:
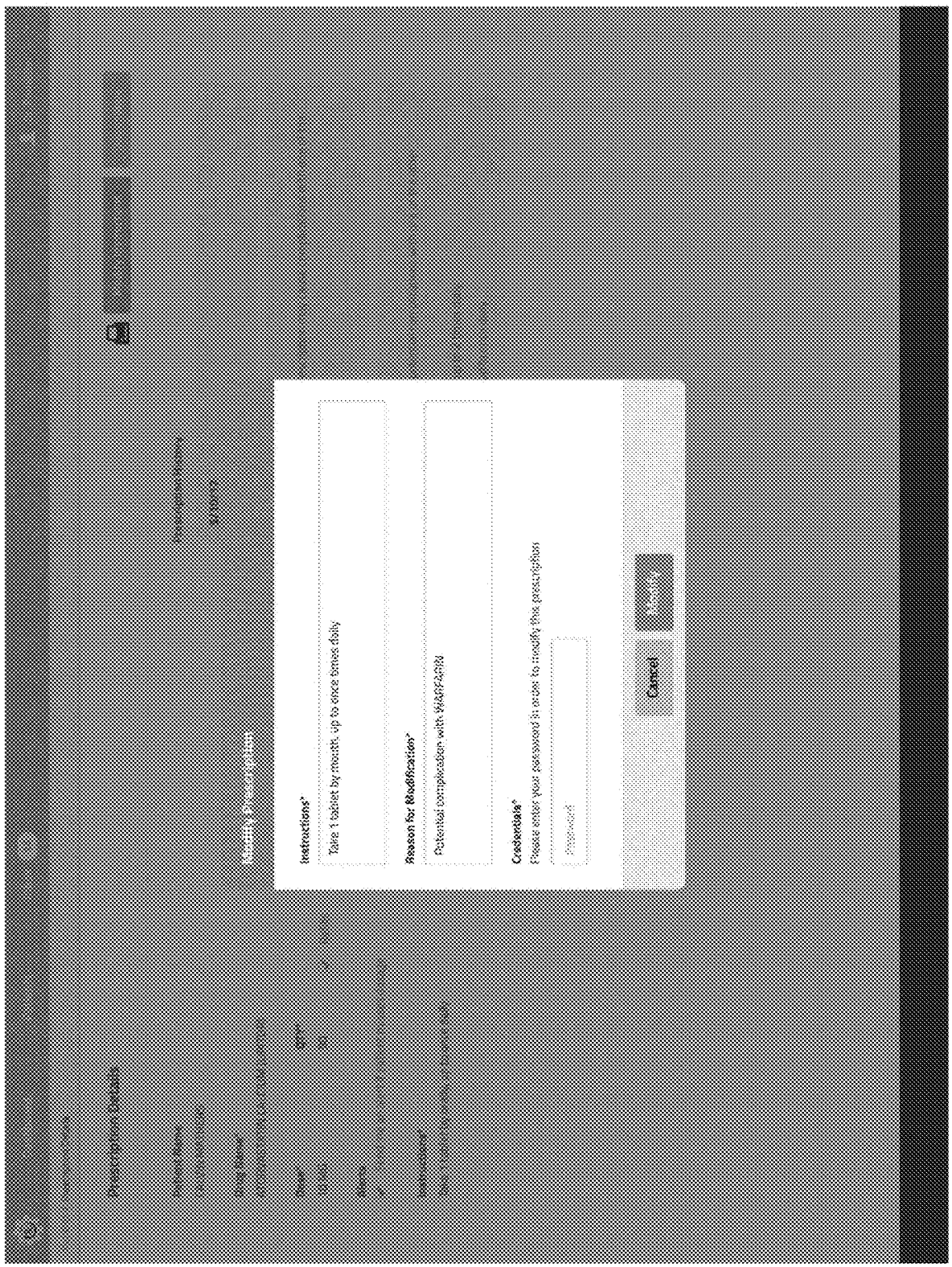
FIGS. 16A-16B show examples of user interfaces of a physician's portal of the medication management platform showing modifications that the user may make to a patient's prescription, according to an aspect.
Figure 16B:
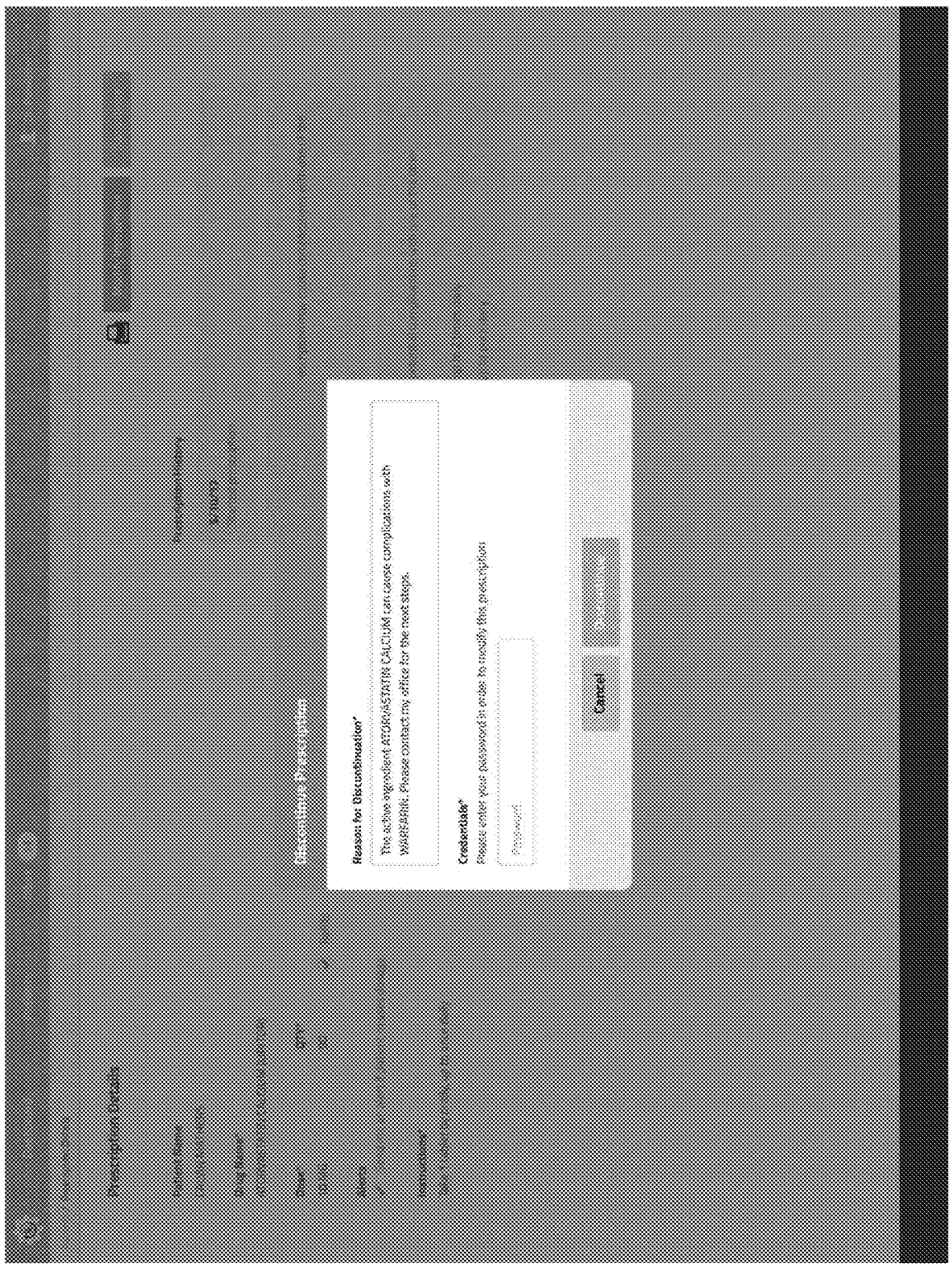

FIGS. 16A-16B show examples of user interfaces of a physician's portal of the medication management platform showing modifications that the user may make to a patient's prescription, according to an aspect. As an example, a doctor using the medication management platform may make changes to a prescription, or may discontinue a prescription. As an example, after discontinuation of a prescription, the tabletop and/or mobile devices may stop alerting or dispensing altogether of the medication, and may also prompt the user to discard the discontinued medication. The user may also include information related to the changes and may be required to provide credentials or authentication in order to make such changes. As another example, the medication management platform may be configured such that a physician cannot see a prescription unless a prescribed user has scanned the prescription into the system.

Figure 17A:
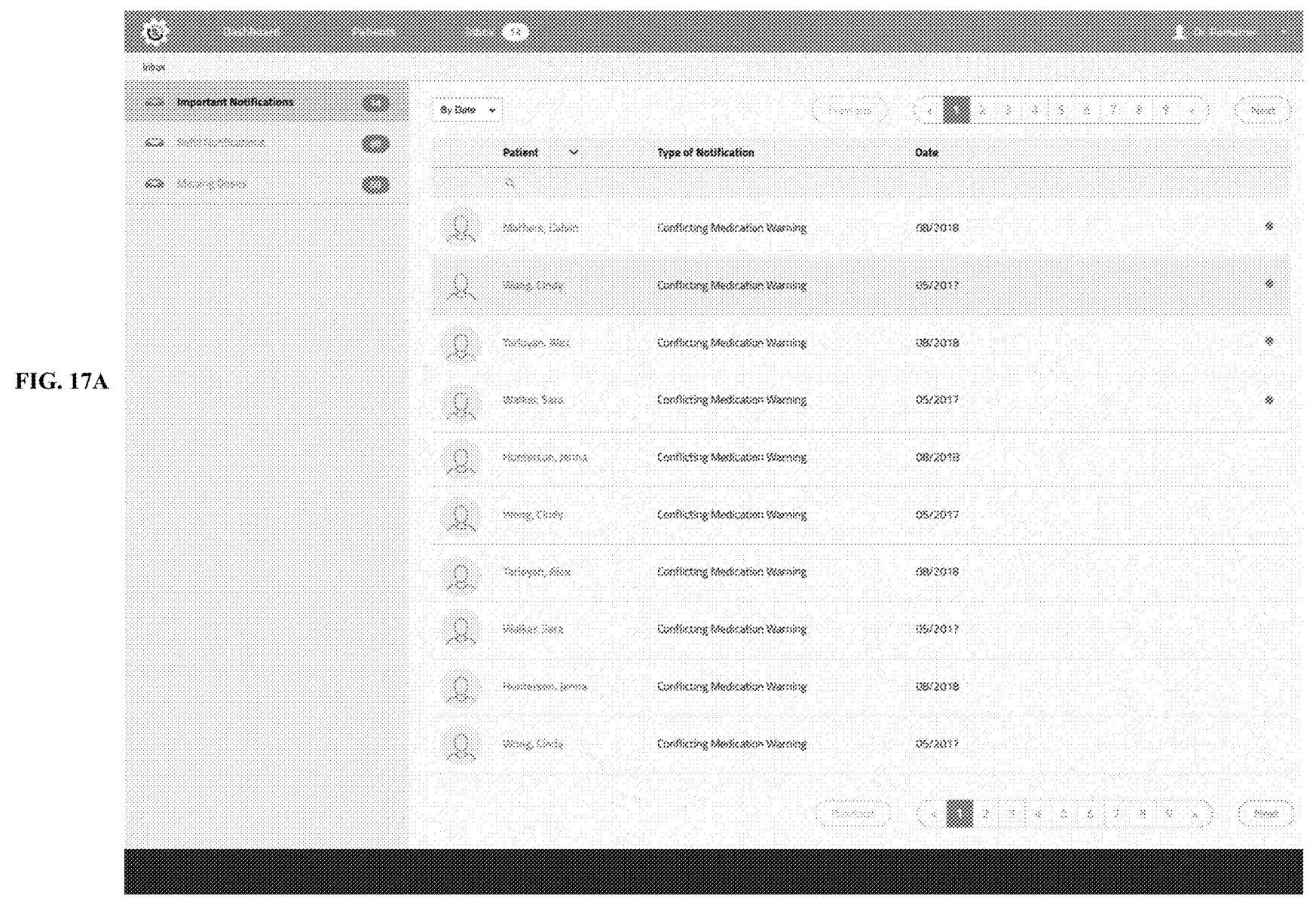
Figure 17B:
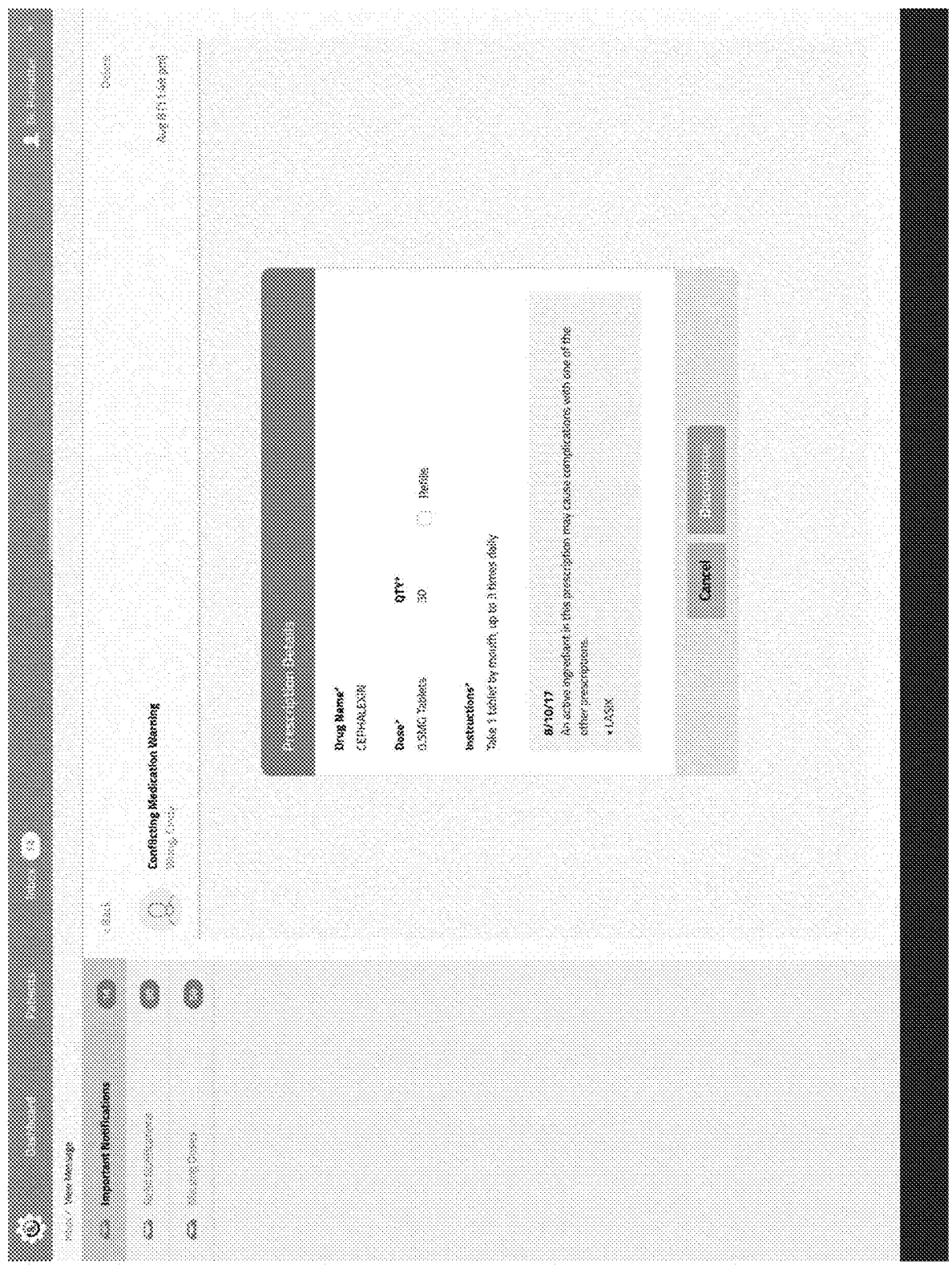

FIGS. 17A-17B show examples of user interfaces of a physician's portal of the medication management platform wherein a medication reconciliation view shows conflicting medication warnings and prescription details to the user, according to an aspect. The medication management platform may allow a user to easily view any conflicting medications before finalizing a prescription, for example. An advantage may be that the information about medication conflicts is easily accessible to the doctor prescribing the medication, and may make necessary changes quickly and efficiently. Another advantage may be that the physician may, as a user, track whether or not the patient is adhering to the physician's instructions.

Figure 18:
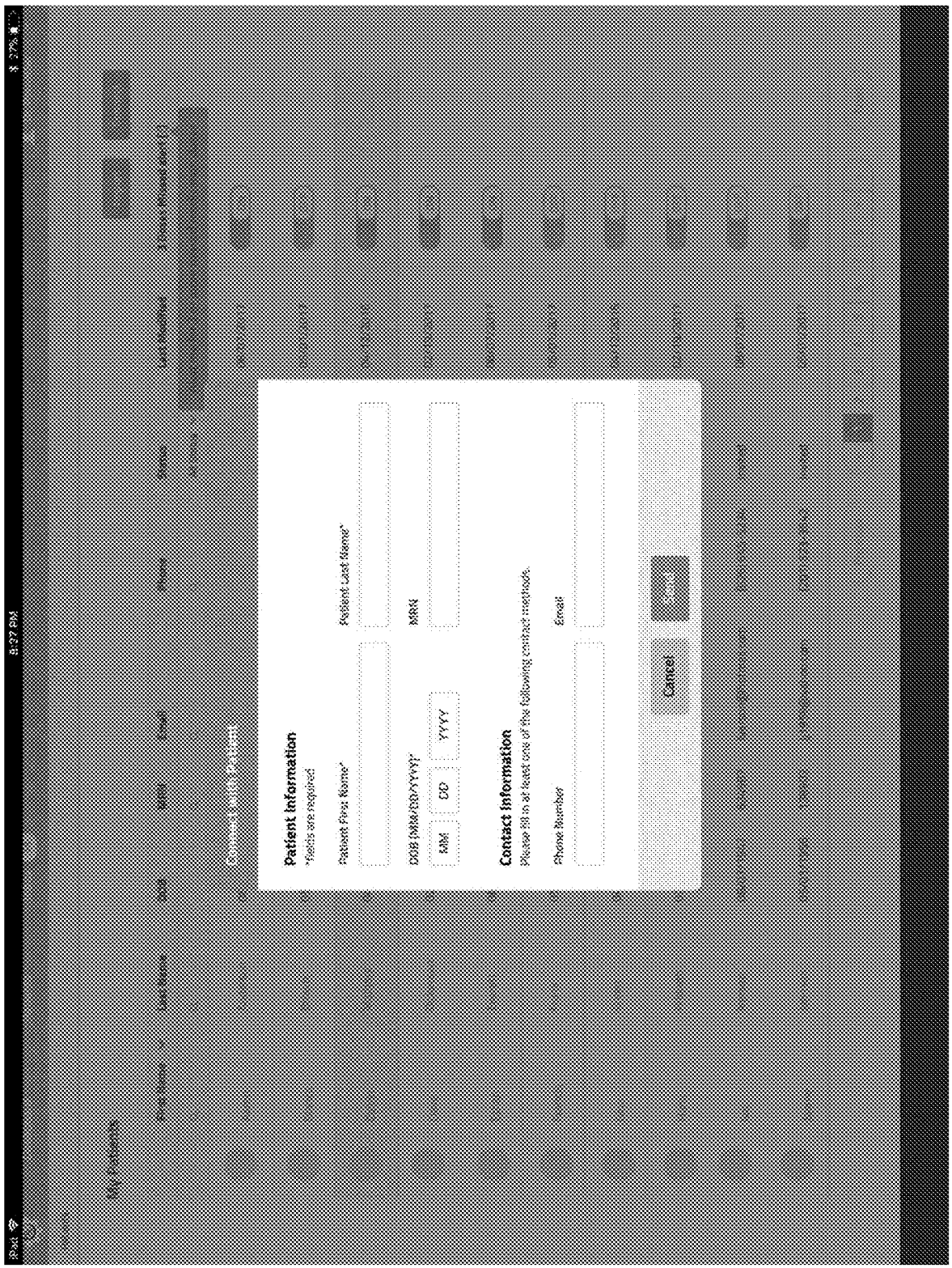
FIG. 18 shows an example of a user interface of a physician's portal of the medication management platform wherein a doctor can easily connect to a patient under their care, according to an aspect.

FIG. 18 shows an example of a user interface of a physician's portal of the medication management platform wherein a doctor can easily connect to a patient under their care, according to an aspect. An advantage may be that a doctor and patient may easily be in contact with one another through the medication management platform. For example, if a change to a patient's prescription must be made, a doctor can easily and quickly contact the patient. As another example, a patient that has questions or concerns about their prescription may quickly and easily contact their doctor. A patient may also similarly contact other users of the medication management platform for social support, for example.

It should be understood that while the focus in the disclosure is on the medication being prescription medication, the medication dispensing apparatus and medication management platform may be used for any other suitable pharmaceuticals, non-prescription or over-the-counter medication, vitamins, dietary supplements, and so on, and thus, any medication regimen that is prescribed or not prescribed may be used and tracked by the medication management system. It should also be understood that while the focus in the disclosure is on the medication being in pill form, the medication or other pharmaceuticals being used with the medication management system may be in a pill, capsule, or tablet form.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A medication management system, comprising a pill dispensing system having:
 a funnel for storing medication, the funnel having:
   an open top end; and
   an open bottom end, wherein the open top end is larger than the open bottom end;
 a tube holder having:
   a first tube holder end;
   a second tube holder end;
   a fin extending between the first tube holder end and the second tube holder end;
   wherein the first tube holder end is associated with a gear wheel;
 a tube having:
   a hollow interior;
   a first tube end;
   a second tube end;
     a channel extending between the first tube end and the second tube end, the channel being configured to receive the fin when the tube slides into the tube holder, and the channel being configured to restrict a side-to-side movement of the tube within the tube holder when the first tube end is aligned with the first tube holder end and the second tube end is aligned with the second tube holder end, such that the tube is secured to the tube holder, and such that a rotational movement of the tube holder causes a same rotational movement of the tube;
   a pill receiving hole between the first tube end and the second tube end, the pill receiving hole facing an upwards direction when the pill dispensing system is not actuated, and the pill receiving hole providing access to the hollow interior;
   wherein the open bottom end is aligned with the pill receiving hole when the pill dispensing system is not actuated, such that the pill receiving hole is configured to receive a pill of the medication from the funnel, and to allow the pill to drop from the funnel into the hollow interior of the tube;
   wherein the tube is removable from the tube holder by sliding the tube in a lengthwise direction away from the tube holder; and
 a rack and pinion actuator for actuation of the pill dispensing system, wherein:
   a rack of the rack and pinion actuator is at least a gear arm;
   a pinion of the rack and pinion actuator comprises the gear wheel; and
   a gear arm actuator is configured to move the pinion, thus causing the rotational movement of the tube holder due to the association of the tube holder with the gear wheel;
 such that the rotational movement causes the pill receiving hole to face a downwards direction and thus dispense the pill housed within the hollow interior out of the pill dispensing system.

2. The medication management system of claim 1, further comprising:
 a medication management platform accessible through an electronic device;
 a medication management platform database for storage of medication information related to a user; and
 means for the pill dispensing system to have internet connectivity and wireless communication capability, such that:
   a medication regimen is sent to the pill dispensing system via a wireless communication to be stored in the medication management platform database;
   the pill dispensing system tracks medication dispensing to create a user record related to the user; and
   the user record is sent to the medication management platform database via the wireless communication, and wherein the user record becomes part of the medication information related to the user.

3. The medication management system of claim 2, wherein the electronic device houses the pill dispensing system, the electronic device being sized to house a single medication bottle; the electronic device comprising:
 a base configured to house the pill dispensing system, the base having:
   a bottom base end;
   a top base end, the top base end being open such that the medication bottle can access and be secured to the funnel;
 a glass cover configured to enclose the pill dispensing system and the medication bottle by locking onto the base; and
 a notification system having means for alerting a user that the pill is to be dispensed according to the medication regimen imported into the medication management system.

4. The medication management system of claim 2, wherein the electronic device comprises a housing for the pill dispensing system and a plurality of medications;
   the electronic device further comprising:
      at least a camera capable of reading a set of written instructions related to the medication regimen;
      a control panel; and
      software configured to store the medication regimen and alert the user via the notification system when a first medication is to be dispensed according to the medication regimen;
      wherein the pill is a pill of the first medication according to the medication regimen;
      means for moving from the plurality of medications the first medication into the pill dispensing system for dispensing the pill of the first medication out of the pill dispensing system.

5. The medication management system of claim 2, wherein the electronic device is a mobile electronic device having an application for accessing the medication management platform.

6. The medication management system of claim 3, wherein the gear arm actuator is a lever accessible from an exterior surface of the base.

7. The medication management system of claim 4, wherein the gear arm actuator is within the housing and electronically controlled via the control panel.

8. The medication management system of claim 2, wherein a second user having credentials for prescribing medication has access to the medication management platform to make changes to the medication regimen.

* * * * *